US011610685B2

(12) United States Patent
Mahoney et al.

(10) Patent No.: US 11,610,685 B2
(45) Date of Patent: *Mar. 21, 2023

(54) METHODS AND SYSTEMS FOR COGNITIVE BEHAVIORAL THERAPY

(71) Applicant: COVIDIEN LP, Mansfield, MA (US)

(72) Inventors: Patrick M. Mahoney, Wallingford, CT (US); Jordan A. Tack, Middleton, WI (US); Haluk Pehlivanoglu, Boulder, CO (US)

(73) Assignee: Covidien LP, Mansfield, MA (US)

( * ) Notice: Subject to any disclaimer, the term of this patent is extended or adjusted under 35 U.S.C. 154(b) by 279 days.

This patent is subject to a terminal disclaimer.

(21) Appl. No.: 16/944,237

(22) Filed: Jul. 31, 2020

(65) Prior Publication Data

US 2020/0365277 A1   Nov. 19, 2020

Related U.S. Application Data

(63) Continuation of application No. 15/887,448, filed on Feb. 2, 2018, now Pat. No. 10,748,660.

(60) Provisional application No. 62/454,380, filed on Feb. 3, 2017.

(51) Int. Cl.
| | |
|---|---|
| *G16H 10/60* | (2018.01) |
| *G16H 50/30* | (2018.01) |
| *G16H 50/70* | (2018.01) |
| *G16H 15/00* | (2018.01) |
| *G16H 20/70* | (2018.01) |

(52) U.S. Cl.
CPC ............. *G16H 50/30* (2018.01); *G16H 10/60* (2018.01); *G16H 15/00* (2018.01); *G16H 20/70* (2018.01); *G16H 50/70* (2018.01)

(58) Field of Classification Search
CPC ...................................................... G16H 10/60
See application file for complete search history.

(56) References Cited

U.S. PATENT DOCUMENTS

| | | | |
|---|---|---|---|
| 8,475,367 | B1 | 7/2013 | Yuen |
| 10,748,660 | B2 | 8/2020 | Mahoney et al. |
| 2006/0001680 | A1* | 1/2006 | Bork ................ H04M 1/72427 345/629 |
| 2013/0310658 | A1 | 11/2013 | Ricks |
| 2014/0089836 | A1 | 3/2014 | Damani |
| 2018/0122517 | A1 | 5/2018 | Bessette |

* cited by examiner

*Primary Examiner* — John A Pauls
(74) *Attorney, Agent, or Firm* — Carter, DeLuca & Farrell LLP

(57) ABSTRACT

Methods and systems are provided for cognitive behavioral therapy. A first set of data and a second set of data related to a health attribute are received, over a first time period. The first and second sets of data are displayed in a first and a second graphical item. A graphical button is displayed on the first graphical item and configured to move it on a display. Using the graphical button, the first graphical item is, at least partially, overlaid upon the second graphical item. In response to the overlaying a third set of data is generated and displayed in a third graphical item. The third set of data is at least partially based on associating the first set of data with the second set of data using one or more sets of rules that establish the relationship between the first set of data and the second set of data.

20 Claims, 9 Drawing Sheets

| | PATIENT | STATUS | CLINIC | START WT. (LBS) | CURRENT WT. (LBS) |
|---|---|---|---|---|---|
| | Mike Daniels | RED | Methodist | 455 | 485 |
| | Kathryn Crawford | RED | Montogomergy General | 423 | 451 |
| | Cindy Redmond | RED | Commonsworth | 350 | 379 |
| | Jose Hernandez | RED | Methodist | 453 | 461 |
| | Jon Vikkerson | RED | Middleton General | 355 | 382 |
| | Amelia Williamson | RED | Methodist | 233 | 461 |
| | Susan Wanota | RED | Riverview Bariatric | 357 | 381 |
| | Jordan Tellekson | RED | Methodist | 299 | 329 |
| | Erin Rivers-Robinson | RED | Methodist | 302 | 327 |
| | Melissa Santigold | RED | Apple Valley Care Center | 312 | 340 |
| | Olivia Michelson | RED | Better Care Partners | 372 | 301 |
| | Charles Rainier | RED | Regents Center | 392 | 426 |
| | Lee Ann Jollet | RED | Methodist | 359 | 380 |
| | Dominique O'neal | RED | Sunnyvale General | 515 | 541 |
| | Justin Van Eckers | RED | Clearwater Valley Health | 421 | 448 |

METHODS AND SYSTEMS FOR COGNITIVE BEHAVIORAL THERAPY

CROSS-REFERENCE TO RELATED APPLICATION

This application is a continuation of U.S. patent application Ser. No. 15/887,448, filed on Feb. 2, 2018, which claims the benefit of the filing date of provisional U.S. patent application Ser. No. 62/454,380 filed on Feb. 3, 2017.

INTRODUCTION

The present disclosure generally relates to methods and systems of providing enhanced user experience for tracking cognitive behavioral therapy. More particularly, the present disclosure relates to methods and systems for customizing protocols for cognitive behavioral therapy.

BACKGROUND

In recent years, the number of devices capable of recording activity data of a user has increased. Moreover, such devices have become more affordable and easier to carry on a user's person. The increased accessibility of such devices may lead one to believe that users of these devices have successfully replaced their unhealthy behaviors with healthy behaviors. However, the data recorded and provided to these users is not sufficient to identify the behavioral changes required to most efficiently improve a user's health. Additionally, clinicians, such as physicians, surgeons, nutritionists, etc., lack sufficient tools, devices, or systems that identify certain behaviors of a user or patient that result in certain effects. The lack of such tools, devices, or systems lead to a user or a patient being provided with inefficient guidance to change their behaviors, resulting in ineffective health improvements, if any.

SUMMARY

According to an aspect of the present disclosure, systems and method are provided that address the above-mentioned needs. In an aspect of the present disclosure, a method for cognitive behavioral therapy is provided. The method includes receiving a first set of data related to a health attribute, wherein the first set of data is received over a first time period. A second set of data related to a second health attribute, wherein the second set of data is received over the first time period. The first set of data related to the health attribute is displayed in a first graphical item. The second set of data related to the health attribute is displayed in a second graphical item. A graphical button is displayed on the first graphical item, wherein the graphical button is configured to move the first graphical item on a display. Using the graphical button, the first graphical item, is at least partially overlaid upon the second graphical item. In response to overlaying the first graphical item, at least partially, upon the second graphical item, a third set of data is generated and the third set of data is displayed in a third graphical item, wherein the third set of data is at least partially based upon associating the first set of data with the second set of data using one or more sets of rules that establish a relationship between the first set of data and the second set of data.

In another aspect of the present disclosure, the first set of data includes measurements corresponding to a first activity associated with the health attribute and the second set of data includes data corresponding to a second activity associated with the health attribute.

In another aspect of the present disclosure, a frequency at which the first set of data is received is different from a frequency at which the second set of data is received.

In another aspect of the present disclosure, the method further includes displaying a fourth graphical item that displays information about a total number of patients and health status for the total number of patients.

In still another aspect of the present disclosure, the method further includes displaying a fifth graphical item that displays a number of patients from the total number of patients who are at risk of experiencing a serious health related event and an associated color.

In still another aspect of the present disclosure, the method further includes displaying a sixth graphical item that displays a number of patients from the total number of patients who are not at risk of experiencing a serious health related event and an associated color.

In still another aspect of the present disclosure, the method further includes determining whether the measurements corresponding to the first activity associated with the first health attribute are below threshold measurements of the first activity associated with the first health attribute. In response to determining that the measurements are below the threshold measurements for the first activity associated with the first health attribute, identify the first activity as a risk factor. Determine whether the measurements corresponding to the second activity associated with the health attribute are below threshold measurements of the second activity associated with the health attribute. In response to determining that the measurements are below the threshold measurements for the second activity associated with the health attribute, identify the second activity as a risk factor.

In still another aspect of the present disclosure, the method further includes displaying a fourth graphical item that indicates generation of an initial protocol. In response to an interaction with the graphical item, generating the initial protocol, wherein the initial protocol includes the first activity, if the first activity is identified as a risk factor, wherein the initial protocol includes the second activity, if the second activity is identified as a risk factor.

In yet another aspect of the present disclosure, the method further includes selecting, for each activity associated with the health attribute included in the initial protocol, a performance goal.

In yet another aspect of the present disclosure, the method further includes determining whether a threshold number of the performance goals are satisfied. In response to determining that the threshold number of the performance goals are not satisfied determining whether the measurements of the activities associated with the health attribute are within a threshold difference of the performance goals selected for the one or more activities. In response to determining that the measurements are not within the threshold difference, reducing performance goals by a second threshold amount, and generating a new protocol including the reduced performance goals.

In yet another aspect of the present disclosure, the method further includes in response to determining that the threshold number of the performance goals are satisfied, determining whether a medical intervention is necessary. In response to determining that the medical intervention is not necessary, determining whether all performance goals are satisfied. In response to determining that all performance goals are satisfied, determining whether the health attribute is within a desired range. In response to determining that the health attribute is not within the desired range, generating a new protocol.

In yet another aspect of the present disclosure, the method further includes in response to determining that all performance goals are not satisfied, generating the new protocol.

In still another aspect of the present disclosure, the method further includes in response to determining that the medical intervention is necessary, scheduling the medical intervention.

In still another aspect of the present disclosure, wherein the medical intervention is a bariatric procedure.

In still another aspect of the present disclosure, the step of generating the new protocol includes determining whether a more aggressive protocol is suitable. In response to determining that the more aggressive protocol is not suitable, identifying at least one new health attribute that is not included in the initial protocol.

In still another aspect of the present disclosure, wherein the step of generating the new protocol includes determining whether a more aggressive protocol is suitable. In response to determining that the more aggressive protocol is suitable, increasing performance goals by a third threshold amount.

In yet another aspect of the present disclosure, the method further includes generating the new protocol with the increased performance goals.

BRIEF DESCRIPTION OF THE DRAWINGS

The above and other aspects, features, and advantages of the present disclosure will become more apparent in light of the following detailed description when taken in conjunction with the accompanying drawings, in which:

FIG. 3 is a graphical user interface displaying graphical items that present information related to one or more patients of a particular group;

FIG. 4 is a graphical user interface displaying graphical items that present data corresponding to an individual patient and the individual patient's health attributes;

FIG. 5 is a graphical user interface displaying graphical items that enable manipulation of one or more graphical items to present information of an individual patient;

DETAILED DESCRIPTION

Figure 1:
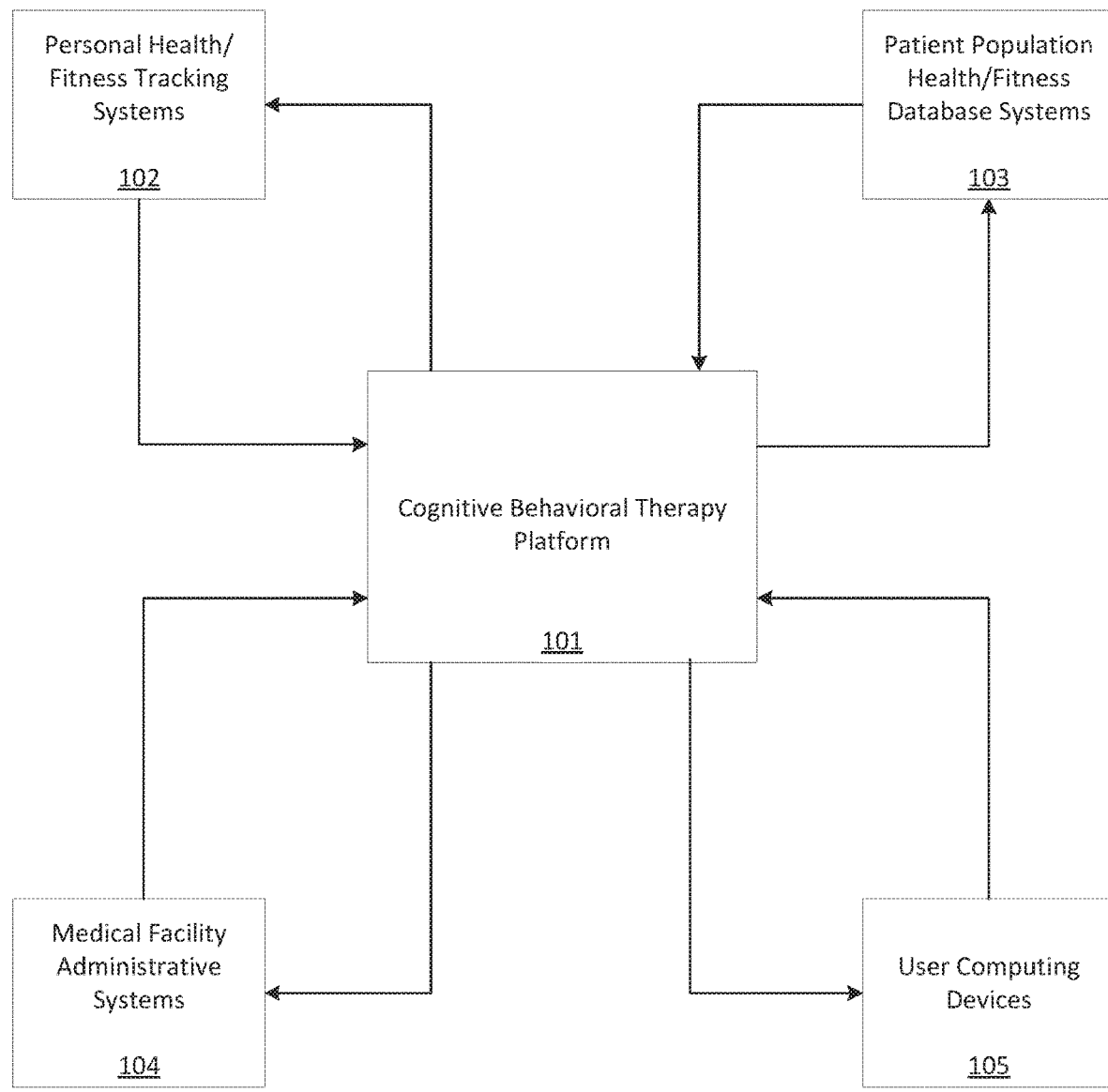
FIG. 1 is a schematic of one illustrative embodiment in accordance with the present disclosure of a cognitive behavioral therapy platform in communication with one or more external systems.

The present disclosure is directed to systems and methods of implementing a healthcare platform that provides cognitive behavioral therapy. In particular, the present disclosure is directed to the use of cognitive behavior therapy for the pre and post-operative assessment and supervision of morbidly obese patients. The morbidly obese often require initial weight loss and overall health status improvement prior to being deemed fit for medical interventions. The present disclosure provides a platform for undertaking pre-operative assessment and identification of a protocol for achieving the weight loss and health status improvements. Using the platform, progress through the protocol can be observed and the protocol altered as necessary to achieve the protocol goals.

The platform described herein generates various protocols, corresponding to various types of medical interventions and/or various groups of patients, based on data from a population of patients that have successfully improved their health status from being morbidly obese. For each protocol, the platform determines performance goals for various activities that have been identified to improve the health status of a morbidly obese patient. The platform associates the protocol with a type of medical intervention, such as a bariatric procedure, and/or physical, medical, geographical, etc., attributes of the population of patients.

Utilizing the platform and the systems and methods described herein, a clinician, using certain physical, medical, or other attributes, of a patient or the medical intervention identified to help the patient, may identify a protocol associated with similar attributes or medical interventions, and if necessary, further customize protocols for each individual patient, based on the individual patient's physical abilities and/or existing health status. The platform determines the individual patient's physical abilities and existing health status, based in part on data received from the individual patient, and assists the clinician in customizing a protocol for the individual patient by recommending performance goals, based in part on the patient's physical abilities and existing health status. The clinician, based on his/her expertise and interactions with the patient, may further customize the protocol.

Additionally, the techniques described herein allow clinicians to identify correlations between one or more activities of a patient and health goal of the patient and customize a protocol based on the identified correlations. Further, the present disclosure provides information on progress or lack thereof to both the patient and the clinicians, as well as identifying which aspects of the protocol achieve success or not, and identifies correlations between individual patients and larger populations of patients sharing at least one attribute in an effort to further enable the customizations of protocols described above. Therefore, by assigning a protocol, created and customized in the manner described above, to a patient, the patient is provided with a plan of action that is easier for the patient to successfully adhere to, and more effective in bringing the health attributes of the patient in line with requirements of a desired medical intervention.

As used herein, the term "clinician" refers to a doctor, a nurse, or any other care provider, including support personnel, or the like, performing a medical intervention. As used herein, the term "health attribute" refers to any information related to health of a patient, including but not limited to, heart rate, body weight, body mass index, etc. Throughout this description, the term "physical attribute" refers to any information related to physical information of a patient, including but not limited to, patient's height, skin color, hair color, eye color, etc. Throughout this description, the term "fitness attribute" refers to any information related to physical activity or inactivity of a patient, including but not limited to, the amount of time spent exercising, the number of steps taken within a certain time period, the number of miles walked within a certain time period, the number of miles ran within a certain time period, etc. Throughout this description, the term "health data" refers to data related to or associated with one or more health attributes of a patient or group of patients. Throughout this description, the term "fitness data" refers to data related to or associated with one or more fitness attributes of a patient or group of patients. Throughout this description, the term "publish" refers to transmitting data to another computing device or making data available for consumption or retrieval by other computing devices. Throughout this description, the term "medical facility" refers to any entity that provides healthcare related services, such as a hospital, a clinic, a medical office, etc.

With reference to FIG. 1, a cognitive behavioral therapy platform 101 communicatively coupled to one or more external computing devices and systems is shown. Examples of the one or more external computing devices and systems, as shown in FIG. 1, include, but are not limited to, personal health and/or fitness tracking systems 102, patient population health and fitness database systems 103, medical facility administrative systems 104, and user computing devices or user medical devices 105.

The personal health and/or fitness tracking systems 102 are devices and systems that are configured to monitor and/or track various health and/or fitness attributes of a user. Examples of such devices and/or systems include step counters, sleep monitors, heart rate monitors, pulse rate monitors, any wearable devices, injectables, swallowable(s), or systems configured to capture one or more activities or inactivity or both of a patient, or any other devices or systems configured to capture and transmit health and activity information. In some embodiments, the personal health and/or fitness tracking systems 102 are configured to automatically transmit any newly captured data associated with health and/or fitness attributes of a user to the cognitive behavioral therapy platform 101. In some embodiments, a user, such as a patient, of the cognitive behavioral therapy platform 101 may initiate the transmission of data associated with health and/or fitness attributes of the user to the cognitive behavioral therapy platform 101. In some embodiments, the cognitive behavioral therapy platform 101 is configured to periodically, for example, every few seconds, minutes, hours, or days, request data associated with health and/or fitness attributes.

The patient population health and fitness database systems 103 are database systems that store data related to health and/or fitness attributes of all patients of a medical facility. For example, a patient population health and fitness database system 103 for medical facility X that has eight different locations will include data related to health and fitness attributes of all patients from each of the eight different locations. The health and fitness data associated with a patient of a medical facility are captured throughout the patient's association with the medical facility. For example, the health and fitness data of patient Y is initially captured when patient Y becomes a patient of the medical facility X, and patient Y's health and fitness data is updated each time patient Y visits the medical facility X or a clinician associated with the medical facility X, or each time patient Y provides his/her health and fitness data to the medical facility X or a clinician of the medical facility X. The cognitive behavioral therapy platform 101 is configured to receive data from the patient health and fitness database systems 103 and store the received data in a memory unit (not shown separately in FIG. 1) or data storage units (not shown separately in FIG. 1). In some embodiments, the cognitive behavioral therapy platform 101 is configured to request for data from the patient health and fitness database systems 103 in response to an input received by the cognitive behavioral therapy platform 101. In some embodiments, the cognitive behavioral therapy platform 101 is configured to automatically request for data periodically, for example, every few seconds, minutes, hours, or days, from the patient health and fitness database systems 103 and store the received data in memory or in the data storage units. In some embodiments, in response to an input to the cognitive behavioral therapy platform 101 requesting certain health and/or fitness data, the cognitive behavioral therapy platform 101 determines whether the necessary data exists in memory or in the data storage units prior to requesting the data from the patient health and fitness database systems 103.

The medical facility administrative systems 104 are systems that assist in various administrative tasks of a medical facility, such as, scheduling of surgeries, booking appointments with various clinicians, patient onboarding, creating, updating or managing of patients' electronic medical records (EMR), etc. The cognitive behavioral therapy platform 101 is configured to communicate with medical facility administrative systems 104 to initiate and manage various administrative tasks for patients of the cognitive behavioral therapy platform 101, including, but not limited to, scheduling of patients' surgeries, scheduling appointments with the clinicians, etc. The cognitive behavioral therapy platform 101 is also configured to access EMR data of a patient to identify biographical information and/or medical history of patients and auto-populate one or more corresponding fields of an electronic profile record of the patient. The user medical devices 105 are computing devices and systems that users of the cognitive behavioral therapy platform 101 use to login and access the cognitive behavioral therapy platform 101. Examples of such computing devices and systems include, but are not limited to, desktop computers, laptop computers, smartphones, tablet computers, mobile computing devices, etc.

The cognitive behavioral therapy platform 101 is an application hosted on an application server computer (not shown separately in FIG. 1) that includes one or more processors (not shown separately in FIG. 1) operably connected to one or more of a memory (not shown separately in FIG. 1). The memory stores instructions to be executed by the one or more processors, and the techniques described herein are performed by the cognitive behavioral therapy platform 101 in response to the one or more processors executing the instructions stored in the memory. The memory may be any type of hardware device used to store data. The memory may be volatile memory, such as random access memory (RAM) (e.g., dynamic random access memory (DRAM), static random access memory (SRAM), etc.). The memory may be non-volatile memory, such as read-only memory (ROM) (e.g., programmable read-only memory (EPROM), electrically erasable programmable read-only memory (EEPROM), non-volatile RAM (NVRAM), etc.). The memory may also be magnetic, optical, or electrical media. The one or more processors may be any type of suitable processor that is adapted to perform or execute the techniques or operations or instructions described herein. For example, the processors may be hardware processors programmed to perform the techniques described herein pursuant to the instructions in firmware, memory, or other storage, or a combination thereof. Similarly, the processors may also be one or more application specific integrated circuits (ASICs), field programmable gate arrays (FPGAs) that are persistently programmed to perform the techniques or operations described herein. The processors may also be a central processing unit (CPU), a digital signal processor (DSP), a microprocessor, or any other device that incorporates hard wired logic or program logic or both to perform the operations or techniques described herein The application server computer is configured to execute procedures or instructions, such as programs, routines, scripts, or other computer executable commands necessary for supporting the cognitive behavioral therapy platform 101 and the techniques described herein. In some embodiments, for load balancing purposes, the application server computer comprises of multiple instances of the cognitive behavioral therapy platform 101 and performs load balancing of the users of the cognitive behavioral therapy platform 101 using the multiple instances of the cognitive behavioral therapy platform 101. In some embodiments, the cognitive behavioral therapy platform 101 includes or is coupled to a HyperText Transfer Protocol (HTTP) server and is configured to serve HyperText Markup Language (HTML) documents that browser programs at computing devices, such as the user medical devices 105, can receive, render, and display.

Figure 6:
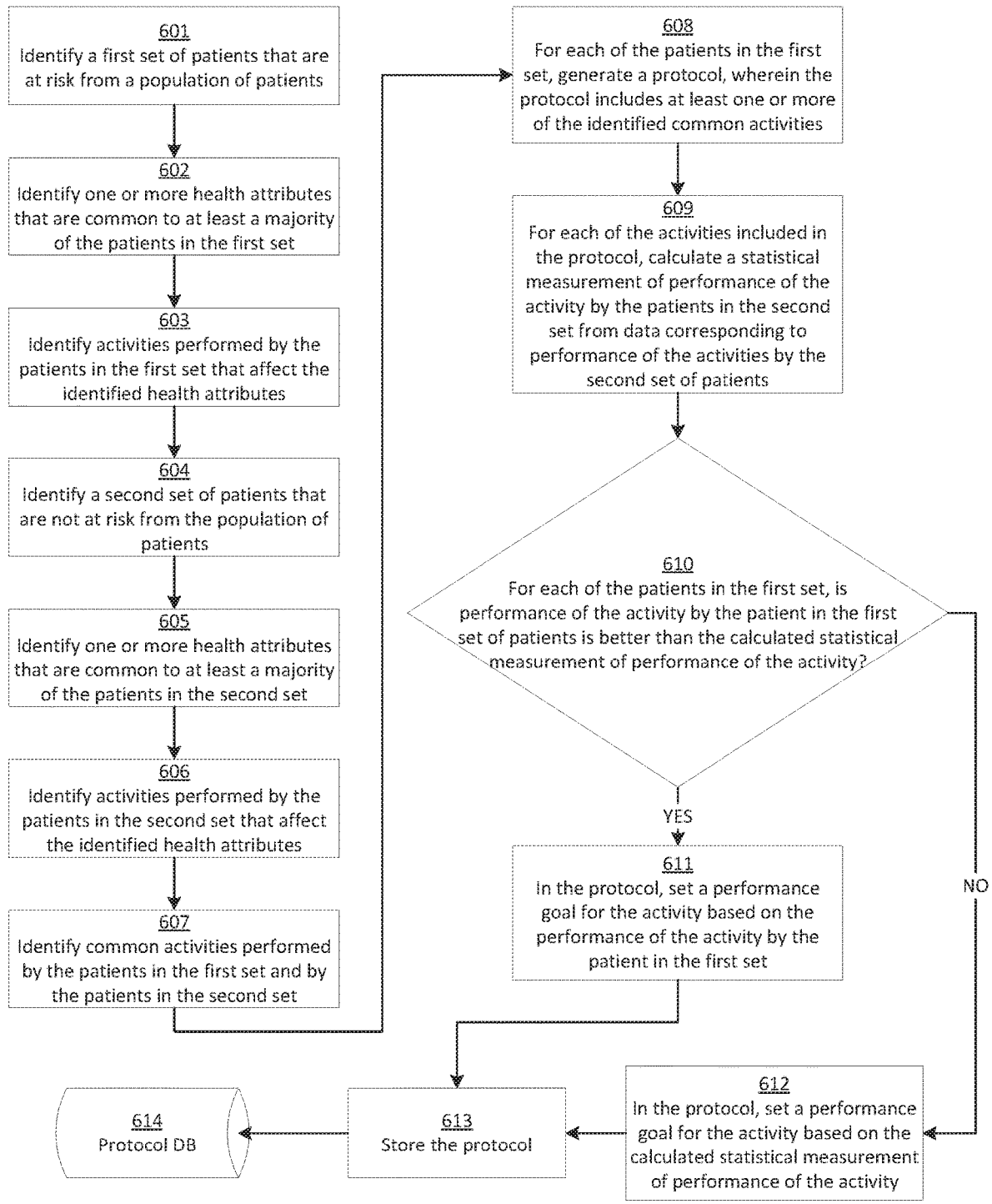
FIG. 6 is a flow chart illustrating the process of generating protocols based on heuristic data.
Figure 7A:
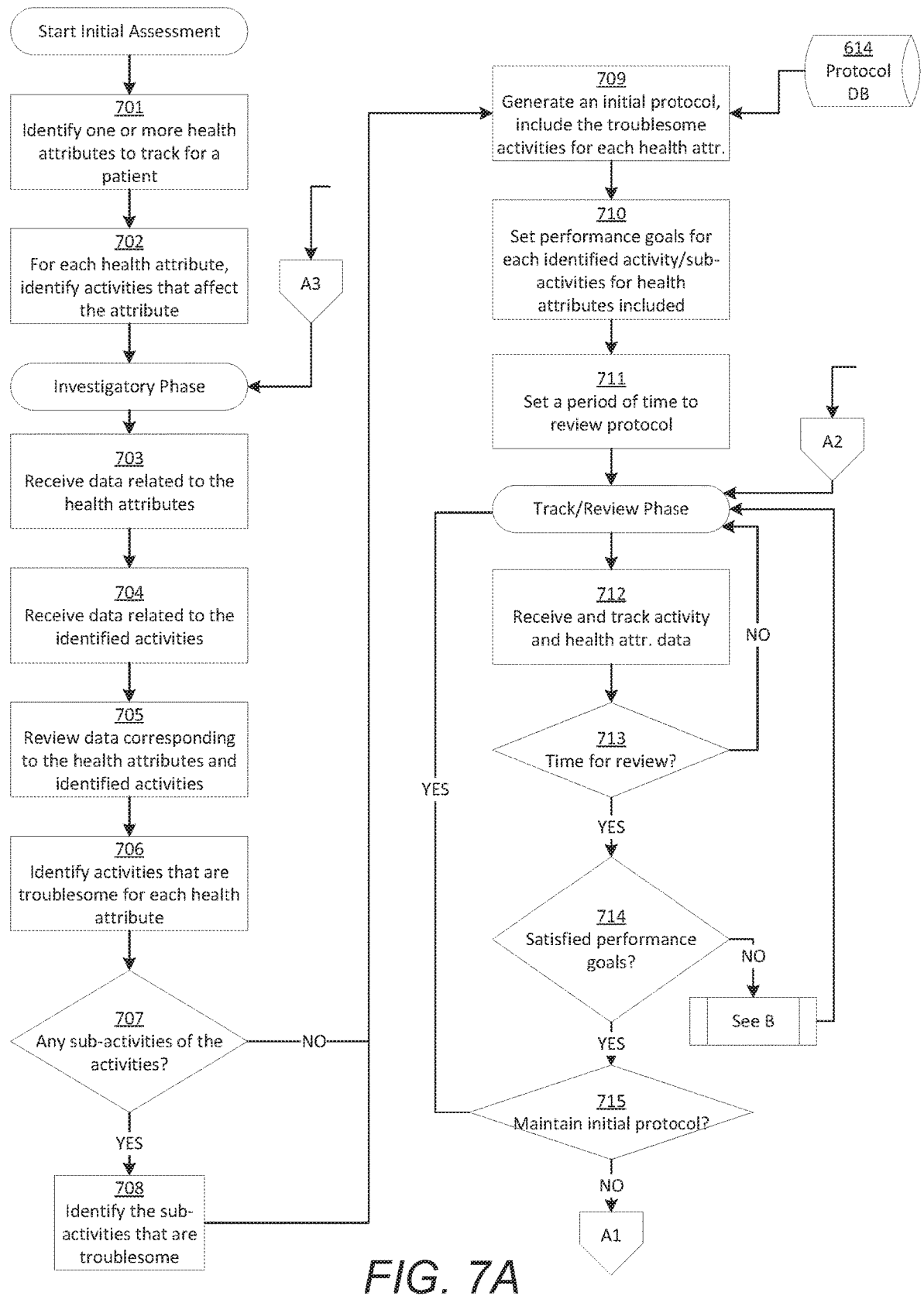
FIG. 7A, FIG. 7B, and FIG. 7C are flow charts illustrating the process of providing a protocol to a patient and tracking performance of a patient.

In accordance with one aspect of the present disclosure, the cognitive behavioral therapy platform 101 is used to identify a protocol that a morbidly obese patient needs to follow in order to be medically cleared for a medical intervention. Where successful, the cognitive behavioral therapy platform can assist in determining whether the medical intervention, such as a bariatric procedure, is appropriate or even required for a patient based on certain activity data of a patient over a certain period of time. The cognitive behavioral therapy platform 101 identifies and selects a protocol for a patient and determines whether a particular medical intervention is required for the patient based on the successful progression of the patient through the selected protocol. As used herein, the term "protocol" refers to a plan of action that includes one or more health attributes, one or more activities, performance goals for the one or more activities, and/or time periods to achieve the performance goals. The cognitive behavioral therapy platform 101 tracks health attributes and performance of the activities of the patient, based in part on data received from the personal health and/or fitness tracking systems 102 of the patient and/or the patient population health and fitness database systems 103. Additional details of identifying and selecting, or generating a protocol for a patient are provided herein in the context of FIG. 6. The cognitive behavioral therapy platform 101 also generates protocols automatically utilizing heuristic data models and data from at least the patient population health and fitness database systems 103. Additional details of generating protocols are provided herein in the context of FIG. 7.

Each user of the cognitive behavioral therapy platform 101 is provided login credentials, such as, a username and a password, and once logged in, the user may interact with the graphical user interface (GUI) (not shown separately in FIG. 1) of the cognitive behavioral therapy platform 101 to utilize the cognitive behavioral therapy platform 101. Users of the cognitive behavioral therapy platform 101 include, but are not limited to, patients and clinicians. Each user of the cognitive behavioral therapy platform 101 is provided certain access privileges. Every functionality of the cognitive behavior therapy platform 101 is associated with a certain access privilege and access to various functionalities of the cognitive behavioral therapy platform 101 is based upon the access privileges of the user and the access privilege associated with the functionality. For example, a user may access a particular functionality if the access privileges of the user include the access privilege associated with the functionality. In some embodiments, the cognitive behavioral therapy platform 101 does not display to a user, functionalities whose associated access privilege is not included within the access privileges of the user.

Functionalities of the cognitive behavioral therapy platform 101 include, but are not limited to, grouping multiple patients into one or more groups based on selected grouping criteria, presenting individual patients within a group, presenting data for one or more health attributes for each patient, presenting data for one or more activities performed by each patient, identifying correlations between multiple attributes, etc. The grouping criteria include, but are not limited to, health, geographical locations, gender, height, weight, etc., of the patients. The data related to the one or more health attributes and the one or more activities performed by a patient are presented across one or more periods of time such as, days, weeks, months, years, etc. In some embodiments, the cognitive behavioral therapy platform 101 limits presentation of data based on the smallest period of time or the slowest frequency at which the data is provided to the cognitive behavioral therapy platform 101. For example, if for a health attribute, data is only provided once a week, then the smallest period of time across which data of that health attribute is presented is weekly or per week. Similarly, if data for a health attribute is provided once a day, then the smallest period of time across which data for that health attribute is presented is daily or per day.

The cognitive behavioral therapy platform 101 presents multiple user interfaces including, but not limited to, a graphical user interface (GUI) (not shown separately in FIG. 1) that allow a user to interact with and access the functionalities of the cognitive behavioral therapy platform 101. The GUI of the cognitive behavioral therapy platform 101 includes one or more graphical items (not shown separately in FIG. 1) using which the user interacts with and provides data and/or instructions to the cognitive behavioral therapy platform 101. Graphical items in a GUI presented by the cognitive behavioral therapy platform 101 are associated with one or more functionalities of the cognitive behavioral therapy platform 101. As used herein, the term "graphical items" includes, but is not limited to, images, graphical labels, data entry mechanisms, such as text boxes, radio buttons, drop down lists, drop down menus, etc., or combinations thereof. The user may also provide data related to health and fitness of the user to the cognitive behavioral therapy platform 101 using one or more graphical items (not shown separately in FIG. 1) that are configured to accept data and/or input from the user in addition to providing health and fitness data to the cognitive behavioral therapy platform 101 using the personal health and/or fitness tracking systems 102 of the user.

In some embodiments, the GUI presented to a user and the graphical items within the GUI that are presented to the user is based on the access privileges of the user and the access privilege associated with the functionality of the graphical items. For example, the access privilege of a patient will be different and more limited than the access privilege of a clinician, such as a physician or a nurse, and at least some of the graphical items presented to the clinician will not be presented to the patient due to the access privileges of the physician and the clinician. The cognitive behavioral therapy platform 101 presents one more data items to a user or causes one or more data items to be displayed to a user based on the inputs received by the cognitive behavioral therapy platform 101. Additional details of the GUI, the graphical items, and the data items displayed or presented to the user are provided herein in the contexts of FIG. 2, FIG. 3, FIG. 4, and FIG. 5.

As described above, a clinician may desire to identify one or more groups of patients that share one or more attributes with an individual patient. The cognitive behavioral therapy platform 101 identifies such groups of patients in response to inputs, such as an input from the clinician specifying the attribute(s) that should be common with the individual patient. The cognitive behavior therapy platform 101 presents the user, such as the clinician, with a user interface configured to receive such inputs. An example of such a user interface is GUI 200B, shown in FIG. 2. The GUI 200b is configured to display graphical items that present information related to one or more groups of patients. The GUI 200b includes navigational graphical items 201a, 201b, 201c, 201d, 201e, collectively navigational graphical items 201. The cognitive behavioral therapy platform 101 is configured to present a particular application screen in response to the selection of a corresponding navigational graphical item. For example, in response to the selection of the navigational graphical item 201a, the cognitive behavioral therapy platform 101 displays application screen 200a (referred to herein as patient dashboard screen 200a), which presents a summary of a set of patients. Similarly, in response to the selection of the navigational graphical item 201b, the cognitive behavioral therapy platform 101 displays application screen 300a (shown in FIG. 3), which presents a list of patients that are included in each of the groups of patients presented in application screen 200a. Additionally, in response to selection of navigational graphical items 201c, 201d, 201e, the cognitive behavioral therapy platform 101 displays application screens that present saved reports, build reports, and a list of clinic locations, respectively. Additional details of reports, generation of reports, and saving of reports are provided herein in context of FIG. 5. As described herein, a graphical item is selected when the cognitive behavioral therapy platform 101 receives an input for the selection of the graphical item. An input for the selection of a graphical item includes, but is not limited to, clicking on the graphical item or touching the graphical item on a touch screen or display of a computing device, such as a smartphone.

Figure 2:
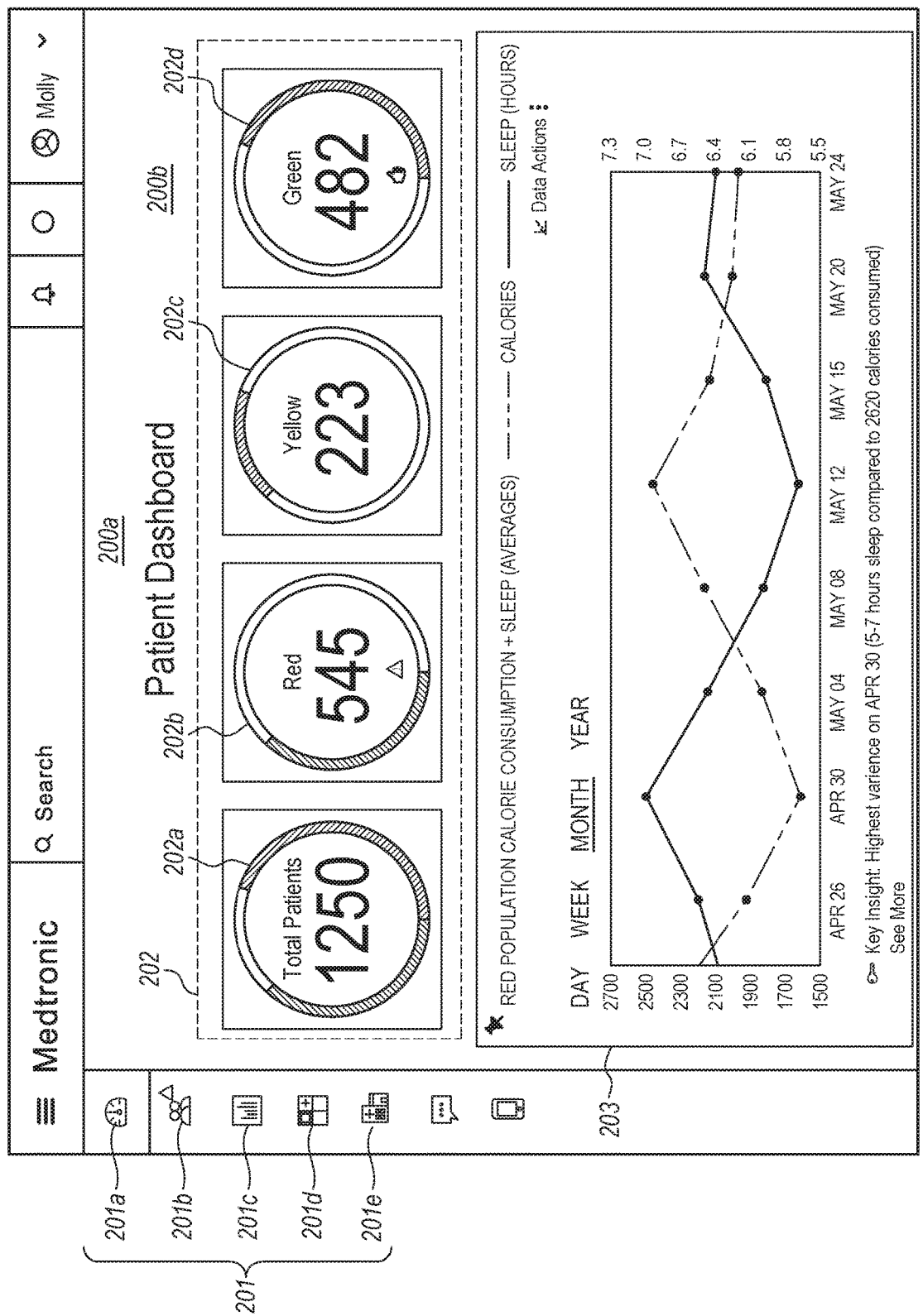
FIG. 2 is a graphical user interface displaying graphical items that present information related to one or more groups of patients.

The cognitive behavioral therapy platform 101 via the patient dashboard screen 200a displays summary information of a set of patients in multiple ways, for instance, as shown in GUI 200b of FIG. 2, by presenting patients in multiple groups and displaying a summarized health indicator for each of the groups. As used herein, a "health indicator" indicates a health level for one or more patients and a health indicator may be represented by any graphical item including, but not limited to, colors, labels, etc. As shown in FIG. 2, health indicator of a set of patients may be represented by multiple colors, such as, red, yellow and green, with each of the colors representing a health level of a group.

As described above, the cognitive behavioral therapy platform 101 receives data related to a number of patients including biographical, geographical, health and fitness data from multiple sources (e.g., the patient population health and fitness database systems 103, the personal health and/or fitness tracking systems 102). The cognitive behavioral therapy platform 101 is configured to group patients and their related data based on one or more grouping criteria. In some embodiments, the cognitive behavioral therapy platform 101 presents multiple grouping criteria to users via graphical items (not shown separately in FIG. 2) configured to display the grouping criteria options and capture user input. The cognitive behavioral therapy platform 101 selects the one or more grouping criteria based on the user input. If multiple grouping criteria are selected, then the multiple grouping criteria may be ordered, based on a default ranking among the grouping criteria. An example of a grouping criterion is to group all patients by the medical facilities that they associated with. Similarly, an example of grouping patients based on multiple grouping criteria is to group patients by a particular medical facility and then by age if the rank of grouping by medical facility is higher than the rank of grouping by age. In some embodiments, the cognitive behavioral therapy platform 101 presents options to the user to select a ranking if multiple grouping criteria are selected.

For each patient, the cognitive behavioral therapy platform 101 determines a health level based on one or more health attributes that are selected to determine the health level and rules that indicate health levels based on the selected health attributes. For example, if body weight is selected as the health attribute to be used in determining a health level for patients, then the cognitive behavioral therapy platform 101 identifies an initial body weight of the patient and the most recent or current body weight of the patient from the health and fitness data received and determines the health level of the patient based on rules that indicate the health level as good health if the current body weight is lower than a threshold amount from the initial body weight of the patient, as neither good health nor poor health if the current body weight is not lower than the threshold amount and not greater than the threshold amount, and as poor health if the current body weight is greater than the threshold amount.

The GUI 200b includes informational graphical items 202a, 202b, 202c, 202d, collectively informational graphical items 202, that present a set of patients that are grouped into multiple groups based on health level of the patients. As used herein, an "informational graphical item" refers to a graphical item that presents data and/or is configured to present more detailed data related to the data initially presented when the graphical item is interacted with by selecting the graphical item, hovering over the graphical item, etc. The informational graphical item 202a displays a total number of patients in the set of patients and a color for each health level of the patients in the set of the patients. Informational graphical item 202b displays a subset of patients of the set of patients that are in poor health and the health level of these patients is indicated by red color. Informational graphical item 202c displays a subset of patients of the set of patients that are in neither poor health nor good health and the health level of these patients is indicated by yellow color, while informational graphical item 202d displays a subset of patients of the set of patients that are in good health and the health level of these patients is indicated by the green color.

In some embodiments, the informational graphical items 202 include rings that are at least partially colored by one or more colors (as shown in FIG. 2). The one or more colors that color the ring or are included in the ring are colors that represent a grouping criteria used to group patients, for instance, a health level of the subset of patients that are grouped into one of the groups presented by informational graphical items 202b, 202c, 202d. Accordingly, the informational graphical item 202a, as shown in FIG. 2, presents a ring that includes all three colors red, yellow, and green because the informational graphical item 202a presents data of all patients in the set of patients, whereas, the information graphical items 202b, 202c, 202d present rings that only include red, yellow, and green colors, respectively, because the information graphical items 202b, 202c, 202d present data for subset of the set of patients that have been grouped into the red, yellow, and green groups, respectively.

In some embodiments, the portion of the rings of the informational graphical items 202 that are colored by a color is based on a statistical measurement of the data used in grouping the set of patients. For example, the portion of the ring of the informational graphical item 202b that is colored red represents the percentage of total patients that have been grouped into group red by the cognitive behavioral therapy platform 101. Similarly, the portions of the ring of the informational graphical item 202a that are red, yellow, and green are proportional to the percentage of total patients that have been grouped into the red, yellow, and green groups, respectively. Likewise, the portion of rings of informational graphical items 202c and 202d that are yellow and green, respectively, are proportional to the percentage of total patients that have been grouped into the yellow and green groups, respectively.

In some embodiments, the informational graphical items 202 display labels indicating the corresponding data presented by the graphical item. For example, the informational graphical item 202a displays the label "Total Patients" to indicate that the data presented by the informational graphical item 202a is for all patients in the set of patients selected. Similarly, informational graphical items 202b, 202c, 202d, display labels "Red", "Yellow", and "Green," respectively, to indicate that the data presented by each of those informational graphical items is only related to patients with corresponding health levels and have been grouped into corresponding groups represented by the informational graphical items 202b, 202c, 202d.

The cognitive behavioral therapy platform 101 displays a list of all patients within the set of patients that were grouped when the informational graphical item 202a is selected. In some embodiments, the cognitive behavioral therapy platform 101 displays a different application screen that presents all patients within the set of patients when the informational graphical item 202a is selected. In some embodiments, the cognitive behavioral therapy platform 101 displays one or more patients within the set of patients when the informational graphical item 202a is hovered over. The number of patients displayed when the informational graphical item 202a is hovered over may be based on configuration data of the cognitive behavioral therapy platform 101 that specifies a threshold number of patients' data to display for informational graphical item 202a. For example, if the configuration data specifies that data for up to the first 3 patients are to be displayed when the informational graphical item 202a is hovered over, then the cognitive behavioral therapy platform 101 displays the first 3 patients of the set of patients that are grouped. Similarly, if the configuration data specifies that data for the last 3 patients are to be displayed when the informational graphical item 202a is hovered over, then the cognitive behavioral therapy platform 101 displays the last 3 patients of the set of patients that are grouped. In some embodiments, the configuration data for the cognitive behavioral therapy platform 101 specifies a default threshold number of patients' data to display for any graphical item of the cognitive behavioral therapy platform 101, and the cognitive behavioral therapy platform 101 displays data for up to the default number of patients, when a corresponding graphical item is hovered over.

The cognitive behavioral therapy platform 101 displays one or more patients that have been grouped into the red group when the informational graphical item 202b is selected or hovered over. In some embodiments, the cognitive behavioral therapy platform 101 displays a different application screen that presents one or more patients that have been grouped in to the red group when the informational graphical item 202b is selected. For example, application screen 300 (shown in FIG. 3) is displayed when the informational graphical item 202b is selected. Configuration data of the cognitive behavioral therapy platform 101 for information graphical item 202b specifies a threshold number of patients, for whom data is to be displayed by the cognitive behavioral therapy platform 101 when the informational graphical item 202b is selected or hovered over. Additionally, the cognitive behavioral therapy platform 101, based on configuration data that specifies a default threshold number of patients data to be displayed, displays data for up to a default threshold number of patients when the informational graphical item 202b is selected or hovered over.

Similarly, the cognitive behavioral therapy platform 101 displays one or more patients of yellow and green groups in response to the selection of the informational graphical items 202c and 202d, respectively. In some embodiments, the cognitive behavioral therapy platform 101 displays an additional application screen that presents one or more patients of the yellow group when the informational graphical item 202c is selected. In some embodiments, the cognitive behavioral therapy platform 101 displays an additional application screen that presents one or more patients of the green group when the informational graphical item 202d is selected.

In some embodiments, the GUI 200b further includes informational graphical item 203 that presents a saved report for one or more of the groups of represented by informational graphical items 202b, 202c, and/or 202d. For example, as shown in FIG. 2, the informational graphical item 203 presents data related to average daily calorie consumption and average daily sleep for all patients within the group represented by informational graphical item 202b. In some embodiments, the cognitive behavioral therapy platform 101 displays the informational graphical item 203 in response to selection of one of the informational graphical items 202 and/or in response to one of the informational graphical items 202 being hovered over. Informational graphical item 203 is similarly interactive as informational graphical items 202. For instance, selection of a different time period, such as day, week, or year, presented by informational graphical item 203 causes the cognitive behavioral therapy platform 101 to display data corresponding to the selected time period.

Turning now to FIG. 3, the cognitive behavioral therapy platform 101 displaying details of multiple patients in tabular form is shown. For the purpose of illustrating a clear example, the same set of patients that were described in the context of FIG. 2 will be used in the context of FIG. 3. As described above, the cognitive behavioral therapy platform 101 displays additional details of patients from a set of patients that are of interest. An example of such a presentation of details is application screen 300a. The application screen 300a presents GUI 300b, which includes the navigational graphical items 201 and informational graphical item 301. The informational graphical item 301 displays, for each patient within the set of patients that are of interest, data related to the additional details of the patient. The additional details of a patient include, but are not limited to, the name, health level, medical facility associated with the patient, one or more health attributes, etc. The cognitive behavioral therapy platform 101 may display the additional details of patients in multiple ways including, but not limited to, bulleted points, lists, and/or tabular form (as shown in FIG. 3).

The informational graphical item 301 is an interactive table and presents data of each patient on a different row of the interactive table. In some embodiments, the cognitive behavioral therapy platform 101 presents one or more options to request data for a different set of patients or subset of patients and displays corresponding data in response to the request. For example, as shown in FIG. 3, the informational graphical item 301 includes graphical items 301f, 301g, 301h, 301i, and the cognitive behavioral therapy platform 101 displays additional details data of patients within the red group, yellow group, or green group, if graphical items 301f, 301g, or 301h, are selected, respectively, and displays additional details data of all patients if graphical item 301i is selected. In some embodiments, the cognitive behavioral therapy platform 101 presents options to sort the displayed data based on data related to one or more types of information. For example, the types of information displayed in FIG. 3 includes patient name, health level of the patient, clinic location of the patient, start weight of the patient, and current weight of the patient, represented by columns labeled "PATIENT," "STATUS," "CLINIC," "START WT. (LBS)," and "CURRENT WT. (LBS)," and the cognitive behavioral therapy platform 101 sorts the rows of the informational graphical item 301 in response to one of columns being selected. In some embodiments, if the displayed data is to be sorted based on multiple types of information, then the cognitive behavioral therapy platform 101 presents options to rank the multiple types of information and sorts displayed data based on the ranking.

In some embodiments each row of the informational graphical item 301 is selectable and the cognitive behavioral therapy platform 101, in response to a row of the informational graphical item 301 being selected, displays additional data for the corresponding patient of the row. For example, if row 301b is selected, then the cognitive behavioral therapy platform 101 displays additional data related to the patient named "Mike Daniels." Similarly, if any of the rows 301c, 301d, or 301e, are selected then the cognitive behavioral therapy platform 101 displays additional data related to patients named "Kathryn Crawford," "Cindy Redmond," and "Jose Hernandez," respectively.

Figure 4:
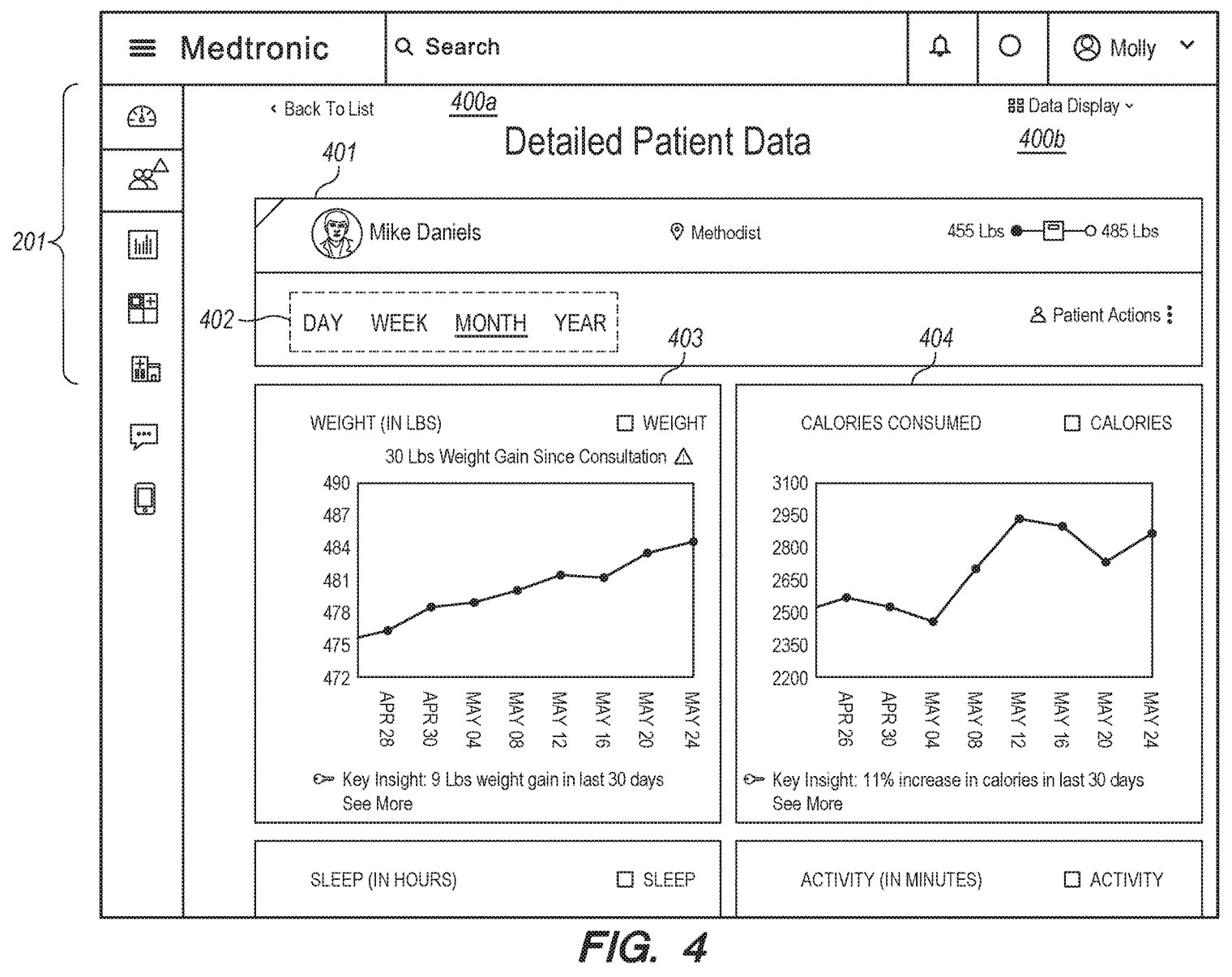

Turning now to FIG. 4, the cognitive behavioral therapy platform 101 displaying data related to information of an individual patient is shown. The cognitive behavioral therapy platform 101 displays data related to an individual patient in response to receiving a request to display the data of the individual patient. The data of the individual patient includes, but is not limited to, biographical data, geographical data, health data, activity data, time periods of when the data was recorded and/or transmitted to the cognitive behavioral therapy platform 101, etc. The request to display data related to information of an individual patient may be sent to the cognitive behavioral therapy platform 101 in multiple ways including, but not limited to, searching for a patient by name or a patient identifier within a search function of the cognitive behavioral therapy platform 101, and/or selecting a patient identifier or patient name, as described above. Application screen 400a is an example of the cognitive behavioral therapy platform 101 displaying data related to information of an individual patient.

The cognitive behavioral therapy platform 101 provides GUI 400b in application screen 400a. The GUI 400b includes navigational graphical items 201 and informational graphical items 401, 402, 403, 404. The informational graphical item 401 presents biographical data, geographical data, and data related to one or more health attributes of the individual patient such as name of the individual patient, the medical facility associated with the individual patient, starting weight of the individual patient, current weight of the individual patient, etc. The informational graphical item 403 presents health data related to body weight, a health attribute, of the individual patient along with a time period over which the health data was recorded and/or transmitted to the cognitive behavioral therapy platform 101. Similarly the informational graphical item 404 presents health data related to calories consumed, an activity, by the individual patient, along with a time period over which the activity data was recorded and/or transmitted to the cognitive behavioral therapy platform 101. The cognitive behavioral therapy platform 101 may display the health and activity data in various forms, such as, tabular form, charts, etc. An example of the cognitive behavioral therapy platform 101 displaying the health and activity data in chart form is shown in FIG. 4 by the informational graphical items 403 and 404.

The cognitive behavioral therapy platform 101 presents options, via the informational graphical item 402, to a user to select a time period over which data in the informational graphical items 403 and 404 are to be presented. For example, in response to selection of "DAY" in the informational graphical item 402, the cognitive behavioral therapy platform 101 displays data related to weight of the patient and calorie consumption by the patient every day for a certain number of days. In some embodiments, the cognitive behavioral therapy platform 101 determines the certain number of days to display data based on the configuration data for the cognitive behavioral therapy platform 101. Similarly, the cognitive behavioral therapy platform 101 displays data presented in the informational graphical items 403 and 404 over a weekly time period, a monthly time period, or yearly time period, in response to selection of "WEEK," "MONTH," or "YEAR" in the informational graphical item 402.

The informational graphical items of the cognitive behavioral therapy platform 101 are selectable and moveable around an application screen of the cognitive behavioral therapy platform 101. For example, informational graphical item 403 may be selected and moved around the application screen 400. The cognitive behavioral therapy platform 101 is configured to initiate one or more its functionalities when an informational graphical item is moved to appropriate portion of the application screen, or when the movement of an informational graphical item is within a sequence of actions that the cognitive behavioral therapy platform 101 recognizes as an input to initiate a particular functionality, or when an information graphical item is partially overlaid on top of another informational graphical item. For example, if the informational graphical item 403 is dragged to the right of the application screen 400a and overlaid, at least partially, on top of informational graphical item 404, then the cognitive behavioral therapy platform will initiate the generation of a new set of health and/or activity data.

The cognitive behavioral therapy platform 101 generates a new set of health and/or activity data for a patient based on the current or historical health, activity, and/or lifestyle behavior data of the patient and data generation rules of the cognitive behavioral therapy platform 101. In some embodiments, the cognitive behavioral therapy platform 101 generates a new set of health and/or activity data for multiple patients or a set of patients based on the current or historical health and/or activity data of the multiple patients or the set of patients and the data generation rules of the cognitive behavioral therapy platform 101. The data generation rules include rules that identify a common time period or time range between the current or historical health and/or activity data being used in generating the new set of health and/or activity data, and the cognitive behavioral therapy platform 101, using the data generation rules, determines the common time period or time range and generates the new set of health and/or activity data for at least the determined common time period or range. In some embodiments, the cognitive behavioral therapy platform 101 receives an input indicating a certain time period or time range for which the new set of health and/or activity data is to be generated and generates the new set of data for the received time period or time range that is equal to or within the determined common time period or range.

The data generation rules of the cognitive behavioral therapy platform 101 also include rules that identify an additional type of health and/or activity data that should be considered in generating the new set of health and/or activity data based on the type of health and/or activity data being used in generating the new set of health and/or activity data. For example, if the cognitive behavioral therapy platform 101 is generating a new set of health and/or activity data based on data related to weight of the patient and calories consumed by the patient, then one or more data generation rules may indicate that sleep data of the patient should also be considered. In some embodiments, the cognitive behavioral therapy platform 101 automatically generates the new set of health and/or activity data based on the additional type of health and/or activity data identified by the rules and the current or historical health and/or activity data of the patient. In some embodiments, the cognitive behavioral therapy platform 101 generates the new set of data based on the current or historical health and/or activity data of the patient and generates a second new set of data based on the additional type of health and/or activity data identified by the rules and the current or historical health and/or activity data of the patient. In some embodiments, the cognitive behavioral therapy platform 101 presents alerts (not shown) to the user regarding the additional type of health and/or activity data identified by the rules and/or presents options (not shown) to the user to select whether or not the additional type of health and/or activity data should be used in generating the new set of health and/or activity data.

The data generation rules of the cognitive behavioral therapy platform 101 further include rules that indicate whether the cognitive behavioral therapy platform 101 should calculate a statistical measurement, such as an average, a variance, a standard deviation, a trend line, etc., from one or more sets of data including the current or historical health and/or activity data of the patient. For example, if the data generation rules of the cognitive behavioral therapy platform 101 indicates that an average sleep time of a patient should be calculated from the sleep time data of the patient when generating a new set of health and/or activity data based on weight and calorie consumption data of the patient, then the cognitive behavioral therapy platform 101 calculates the average sleep time of the patient from the sleep time data and presents the average sleep time data along with the generated new set of health and/or activity data. In some embodiments, the cognitive behavioral therapy platform 101 requests input from a user prior to calculating a statistical measurement and calculates the statistical measurement in response to receiving a confirmation to calculate the statistical measurement.

Figure 5:
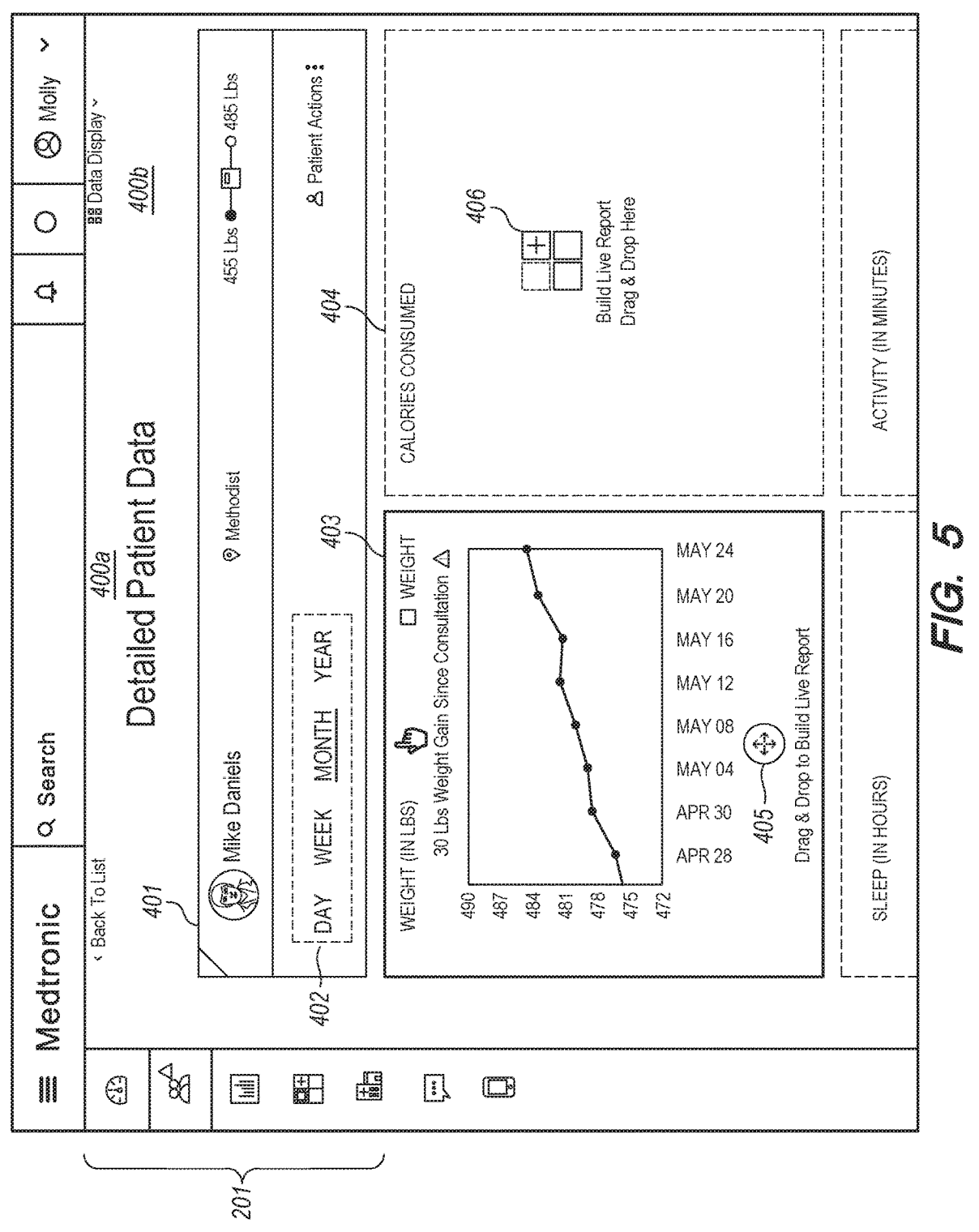

An example of the cognitive behavioral therapy platform 101 initiating the generation of a new data set of health and/or activity day in response to selecting an informational graphical item and overlaying the selected informational graphical item on another informational graphical item is shown in FIG. 5. In response to the selection of an informational graphical item, the cognitive behavioral therapy platform 101 displays a graphical icon on or near the selected informational graphical item that indicates that the selected informational graphical item may be moved around the application screen. For example, as shown in FIG. 5, the cognitive behavioral therapy platform 101 display graphical icon 405 at the bottom of the informational graphical item 403 to indicate that the informational graphical item 403 is ready to be moved around the application screen. In some embodiments, for informational graphical items that are not configured to be moved around an application screen, the cognitive behavioral therapy platform 101 does not display the graphical icon that indicates that the selected informational graphical item may be moved around the application screen.

In response to the selection of an informational graphical item, the cognitive behavioral therapy platform 101 also displays a graphical icon at or near destination locations on the application screen, where moving the selected informational graphical item, including overlaying the selected informational graphical item, on or near the destination locations, causes the cognitive behavioral therapy platform 101 to initiate a functionality of the cognitive behavioral therapy platform 101. For example, in FIG. 5, in response to the selection of the informational graphical item 403, the cognitive behavioral therapy platform 101 displays graphical icon 406 over the informational graphical item 404 and if the informational graphical item 403 is moved to or near the location of the graphical icon 406, then the cognitive behavioral therapy platform 101 initiates the generation of a new set of health and/or activity data. The data upon which the new set of health and/or activity data is generated is the data associated with the informational graphical items used in initiating the generation of the new set of health and/or activity data. For example, the cognitive behavioral therapy platform 101 generates a new set of health and/or activity data for the patient based on the weight and the calorie consumption data of the patient because weight data is the data associated with the informational graphical item 403 and the calorie consumption data is the data associated with the informational graphical item 404. In some embodiments, prior to generating a new set of health and/or activity data of a patient, the cognitive behavioral therapy platform 101 presents options to confirm or cancel generation of the new set of health and/or activity data to a user and generates the new set of health and/or activity data in response to receiving a confirmation to generate the data.

The cognitive behavioral therapy platform 101 displays the newly generated set of health and/or activity data in an informational graphical item (not shown) and presents the informational graphical item on the application screen. The cognitive behavioral therapy platform 101 stores the newly generated set of health and/or activity data in a data storage unit operably coupled to the cognitive behavioral therapy platform 101. The cognitive behavioral therapy platform 101 includes the newly generated set of health and/or activity data with the privileges of the patient and/or the clinician, so that the patient and/or the clinician is able to retrieve the data whenever the patient accesses the cognitive behavioral therapy platform 101. In some embodiments, the cognitive behavioral therapy platform 101 generates and saves a report that includes the newly generated set of health and/or activity data, and sets the privileges of the saved report to include the privileges of the patient and/or the clinician.

Utilizing the newly generated set of health and/or activity data by the cognitive behavioral therapy platform 101, a clinician may identify one or more health attributes and/or activities that affect the health of a patient at risk and/or one or more activities that reduce the risk posed by the identified health attributes. For example, the newly generated set of health and/or activity data may indicate that while the patient's calorie consumption and physical activity on average are satisfactory, the patient is in fact consuming more calories on days he/she engages in increased physical activity and reduces calories on days he/she is less physically active, thereby effectively cancelling out most, if not all, benefits of reducing calorie consumption and increasing physical activity. In some embodiments, the cognitive behavioral therapy platform 101, based on stored rules, displays data related to one or more activities (related activity data) that impact the activities and/or health attributes associated with the newly generated set of health and/or activity data. For example, if the newly generated set of health and/or activity data is related to body weight and physical activity performed over a period of time, then the cognitive behavioral therapy platform 101 may also present data related to number of hours the patient slept during that period of time, if a stored rule indicates that sleep impacts weight loss or performance of physical activity. In some embodiments, the cognitive behavioral therapy platform 101 allows a user, such as a clinician, to manipulate the related activity, for instance, by selecting data points on a graphical item and moving the data points to increase or decrease the data values, and in response, displays changes in the newly generated set of health and/or activity data, based on rules that account for the changes in the related activity data and predict changes in the newly generated set of health and/or activity data based on the changes in the related activity data.

As described above, the cognitive behavioral therapy platform 101 generates protocols for patients, and the clinician may customize one of the generated protocols based on the newly generated set of health and/or activity data. A clinician may also create a new protocol in part based on the newly generated set of health and/or activity data described above. Furthermore, utilizing the protocols and the cognitive behavioral therapy platform 101, a clinician may be assisted in deciding whether or not to recommend a medical intervention, such as a bariatric procedure, for a patient. Additional details of generating protocols by the cognitive behavioral therapy platform 101 and determining whether a medical intervention is necessary for a patient is provided in the contexts of FIG. 6 and FIG. 7.

As described above, the cognitive behavioral therapy platform 101 generates, based on data from a population of patients, one or more protocols for various types of medical interventions and/or for various types of overweight, obese, or morbidly obese patients. An example method of the cognitive behavioral therapy platform 101 generating protocols in such a manner is method 600, shown in FIG. 6. In some embodiments, the cognitive behavioral therapy platform 101 is configured to automatically generate protocols at a specified time, for instance, at a particular day and/or time of a week, month, etc. In some embodiments, the cognitive behavioral therapy platform 101 is configured with batch jobs and/or processes that are configured to execute at a specified and the batch jobs and/or processes initiate the generation of protocols by the cognitive behavioral therapy platform 101. Each protocol generated by the cognitive behavioral therapy platform 101 addresses at least one type of health risk, such as, obesity. In some embodiments, the cognitive behavioral therapy platform 101 generates multiple protocols for a health risk and each of the multiple protocols is different from the others and is targeted for a set of patients that share a common biographical, geographical, and/or physical trait.

In step 601, the cognitive behavioral therapy platform 101 identifies a first set of patients whose health level is at risk, from a population of patients. The risk faced by the first set of patients may be any type of a health risk such as diabetes, metabolic disease, obesity, heart disease, etc. As described above, the cognitive behavioral therapy platform 101 receives health and activity data of patients from a multiple sources and may group the patients based on grouping criteria. The cognitive behavioral therapy platform 101 identifies the first set of patients whose health level is at risk by grouping patients based on one or more health attributes that contribute to the health risk. The cognitive behavioral therapy platform 101 identifies the health attributes that contribute to a health risk based on rules for protocol generation that indicate the contributing health attributes for a health risk. The contributing health attributes may be ranked and the cognitive behavioral therapy platform 101, in identifying the first set of patients that are at risk, may utilize only those health attributes that are above a certain threshold rank. For example, if the protocol being generated is for obesity, the health risk, and the rules indicate that body weight is a contributing health attribute for the risk of obesity and the threshold rank that should be used in identifying the first set of patients at risk is the highest rank, then the cognitive behavioral therapy platform 101 groups the population of patients based on body weight of the patients and identifies, from the population of patients, those patients whose body weight indicates that they may be at risk of being obese or are obese.

In step 602, the cognitive behavioral therapy platform 101 identifies one or more health attributes that are common to at least a majority of the patients in the first set. In identifying the health attributes that are common to a majority of the patients in the first set, the cognitive behavioral therapy platform 101 may also identify additional health attributes that were not used in identifying the first set of patients. For example, if the rules also indicate that high body fat percentage above a threshold percentage is also a contributing health attribute to obesity, then the cognitive behavioral therapy platform 101 determines whether the body fat percentage is above the threshold percentage for at least a majority of the patients in the first set, and if body fat percentage is above the threshold for at least the majority of the patients in the first set, the cognitive behavioral therapy platform 101 identifies body fat percentage as one of the health attributes that are common to at least the majority of the patients in the first set. In some embodiments, the cognitive behavioral therapy platform 101 updates the rankings of the contributing health attributes of a health risk using machine learning techniques. In some embodiments, the cognitive behavioral therapy platform 101 is provided with research data on various medical issues and the cognitive behavioral therapy platform 101, using machine learning algorithms that are trained to identify changes in health attributes that contribute to a health risk, update the rankings of the health attributes that contribute to the health risk. For example, if the cognitive behavioral therapy platform 101 identifies from the provided research data that body fat percentage is a more accurate indicator than body weight, then the cognitive behavioral therapy platform 101 updates the rank of body fat percentage to be greater than the rank of body weight for health attributes that contribute to obesity.

In step 603, the cognitive behavioral therapy platform 101 identifies one or more activities performed by the patients in the first set that affect health attributes identified in step 602. The rules for protocol generation indicate activities that affect a health attribute. In some embodiments, the cognitive behavioral therapy platform 101 determines whether an activity is performed by a patient based on whether data related to the patient performing the activity was provided to the cognitive behavioral therapy platform 101. In some embodiments, if the activity is a well-known activity, such as, calorie consumption, sleeping, exercising, etc., then the cognitive behavioral therapy platform 101 identifies the activity as performed by the patient even if data related to the patient performing the activity was not provided to the cognitive behavioral therapy platform 101.

In step 604, the cognitive behavioral therapy platform 101 identifies, from the population of patients, a second set of patients that are not at risk of the health risk for which the protocol is being generated. The cognitive behavioral therapy platform 101 identifies the second set of patients by identifying the patients among the population of patients whose health attributes that contribute to the health risk do not indicate that the patient is at risk for the health risk. For example, the cognitive behavioral therapy platform 101 identifies patients whose body weight does not indicate that they are at risk of obesity. In step 605, the cognitive behavioral therapy platform 101 identifies one or more health attributes that are common to at least a majority of the patients in the second set. The cognitive behavioral therapy platform 101 identifies the one or more health attributes for the second set of patients using methods and techniques provided in context of step 602.

In step 606, the cognitive behavioral therapy platform 101 identifies activities performed by the patients in the second set that affect the identified health attributes. The cognitive behavioral therapy platform 101 identifies activities performed by the patients in the second set using methods and techniques provided in context of step 603. In step 607, the cognitive behavioral therapy platform 101 identifies activities that are common among the activities performed by the first set of patients and the second set of patients. In some embodiments, if a well-known activity to the general public, such as cycling, is identified as being performed by the second set of patients but not by the first set of patients, then the activity is still identified as a common activity performed by the first set of patients and the second set of patients since the activity is sufficiently well-known to the general public that the first set of patients will not have any obstacles in learning the activity and may begin performing the activity once the protocol is assigned to them.

In step 608, for each of the patients in the first set, the cognitive behavioral therapy platform 101 generates a protocol that includes at least one or more of the identified common activities. In some embodiments, the cognitive behavioral therapy platform 101 further groups the patients in the first set based on physical and/or geographical attributes, such as, age or a range of ages, height or range of heights, geographical location, ethnicity, family medical history, etc., of a patient and generates protocols per group of patients in the first set. In step 609, the cognitive behavioral therapy platform 101, for each of the activities included in the protocol, calculates a statistical measurement of the performance of the activity by the patients in the second set based on data corresponding to the performance of the activities by the patients in the second set.

The statistical measurements that are calculated are based on rules that indicate the statistical measurements to calculate for an activity, for example, a rule that indicates that calculation of average calorie consumption over a period of time. In some embodiments, the cognitive behavioral therapy platform 101 calculates the statistical measurements based on performance data of all patients in the second set. In some embodiments, if the protocols are generated per group of patients in the first set, then the cognitive behavioral therapy platform 101 customizes the protocol for the group by calculating the statistical measurements based on performance data of patients in the second set that share the same physical and/or geographical attributes with the patients in the group. For example, if patients in the first set are grouped based on range of ages, resulting in two groups of patients within an age range of 30 to 35 years (group A) and 40 to 45 years (group B), then the cognitive behavioral therapy platform 101, in calculating the statistical measurements, identifies patients in the second set that also are within or close to the age range of group A patients and calculates statistical measurements based on performance data of patients in the second set that are within or close to the age range of group A patients.

In step 610, the cognitive behavioral therapy platform 101 determines, for each of the patients in the first set, for each of the activities included in the protocol, whether the performance of the activity by the patient is better than the calculated statistical measurement of the performance of the activity. The cognitive behavioral therapy platform 101 identifies the performance of the activity based on performance data of the patient. If the performance of the activity by the patient is better than the calculated statistical measurement, then in step 611, the cognitive behavioral therapy platform 101 sets a performance goal for the activity based on the performance of the activity by the patient in the first set. The cognitive behavioral therapy platform 101 may set a performance goal by adjusting the performance of the activity by the patient by a threshold amount indicated by rules for setting performance goals. For example, if the activity is calorie consumption and the daily average calorie consumption by the patient is better than the daily average calorie consumption by the patients in the second set and the protocol generation rules indicate that threshold amount to reduce the calorie consumption by is ten percent, then the cognitive behavioral therapy platform sets the calorie consumption goal for the patient by reducing the daily average calorie consumption of the patient by 10 percent. If the performance of the activity by the patient is not better than the calculated statistical measurement, then in step 612, the cognitive behavioral therapy platform 101 sets a performance goal for the activity based on the calculated statistical measurement of the performance of the activity.

In step 613, the cognitive behavioral therapy platform 101 stores the generated protocol in a data storage unit, such as protocol database 614. In some embodiments, the cognitive behavioral therapy platform 101 also makes the generated protocol accessible to the patient. For example, the cognitive behavioral therapy platform 101 includes the generated protocol within the privileges of the patient, so that the patient may access the protocol. The cognitive behavioral therapy platform 101 also makes the generated protocol accessible by a clinician. In some embodiments, the cognitive behavioral therapy platform associates each generated protocol with a physical attributes, geographical attributes, and/or ethnicity of the patient in order to make the generated protocol retrievable by a clinician who is searching for a protocol for a patient with similar physical attributes, geographical attributes, and/or ethnicity as the patient associated with the protocol. For example, a clinician consulting a 24 year old patient at risk for obesity may use the cognitive behavioral therapy platform 101 to search for protocols generated for obesity for other patients who were 24 years old or near that age and associate one of those protocols with the 24 year old patient. The clinician may further customize the protocol associated with the 24 year old patient based on one or more observations, as shown in FIG. 7.

With the generation of protocols, a clinician is provided with at least a starting protocol for a type of medical intervention that may be further customized, if necessary based on the clinician's expertise and interactions with an individual patient. In identifying portions of the protocol to customize, the clinician may rely upon the cognitive behavioral therapy platform 101 to identify the protocol and base his/her customizations off the recommendations and/or customizations of the cognitive behavioral therapy platform 101. An example of the cognitive behavioral therapy platform 101 identifying a protocol and recommending/customizing the protocol based on the cognitive behavioral therapy platform 101 is shown by method 700 in FIG. 7A, FIG. 7B, and FIG. 7C.

The method 700 depicts preparing a morbidly obese patient for a medical intervention, such as bariatric procedure, using cognitive behavioral therapy platform 101 in accordance with the present disclosure. As part of this preparation, the method 700 includes a determination of whether a medical intervention remains necessary for the patient after following a protocol established using cognitive behavioral therapy platform 101. During the initial assessment phase, in step 701, shown in FIG. 7A, one or more health attributes are identified to track for a patient by the cognitive behavioral therapy platform 101. The cognitive behavioral therapy platform 101 identifies one or more health attributes for a patient in response to receiving an input related to a medical intervention that the patient and his/her clinician desires for the patient to undergo. While the clinician and the patient may agree on a particular medical intervention that the patient should undergo, the clinician may still wish to determine whether the patient is ready for such a medical intervention or determine whether alternatives to the medical intervention are available. For example, the clinician and the patient may desire that the patient to undergo a bariatric procedure, however, prior to scheduling the bariatric procedure, the clinician should determine whether the patient is ready for such a procedure or whether alternatives to a bariatric procedure are available for the patient, or whether the bariatric procedure will actually improve the health of the patient. The cognitive behavioral therapy platform 101 identifies the one or more health attributes to track based on the input specifying the medical intervention and/or stored medical intervention rules that indicate one or more health attributes for each medical intervention.

In step 702, the cognitive behavioral therapy platform 101, for each identified health attribute, identifies one or more activities that affect the health attribute. The cognitive behavioral therapy platform 101 identifies the activities based on the rules described above that indicate the one or more activities for a health attribute. In some embodiments, the clinician reviews the health attributes identified in step 701 and the activities identified for each health attribute in step 702, and adds additional health attributes and corresponding activities that affect the attributes, and/or deletes one or more health attributes and corresponding activities. In some embodiments, if the patient does not have a profile with the cognitive behavioral therapy platform 101, then the cognitive behavioral therapy platform 101 displays an alert indicating that the patient does not have a profile with the cognitive behavioral therapy platform 101 and/or that the patient is not registered as user of the cognitive behavioral therapy platform 101 and prompts the user to register and/or generate a profile for the patient. Registering and/or generating a profile for the patient includes creating and storing a username and a password for the patient along with the privileges for access to the various functionalities of cognitive behavioral therapy platform 101 and data accessible the cognitive behavioral therapy platform 101. In some embodiments, the personal health and/or fitness tracking systems 102 and user medical devices 105 of the patient are also registered with the cognitive behavioral therapy platform 101 in order to exchange communications and/or data between the personal health and/or fitness tracking systems 102 of the patient and user medical devices 105 of the patient and the cognitive behavioral therapy platform 101.

After the initial health attributes and corresponding activities are identified, during the investigatory phase, in step 703, the cognitive behavioral therapy platform 101, receives data related to the identified health attributes. For example, if the health attribute identified step 701 for the patient is weight, then in step 703, the cognitive behavioral therapy platform 101 receives data related to the weight of the patient. Other health attributes to track may include body mass index (BMI), body fat percentage, cholesterol, blood sugar, and a number of additional health related attributes of the patient. In step 704, the cognitive behavioral therapy platform 101, receives data related to the identified activities. For example, if the activities identified for weight are physical activity, calorie consumption, and sleep hours, then in step 704, the cognitive behavioral therapy platform 101 receives data related to physical activity, calorie consumption, and sleep hours of the patient.

Data for a health attribute or an activity is received by the cognitive behavioral therapy platform 101 at a frequency. The frequency may be set individually for each health attribute. The cognitive behavioral therapy platform 101 is configured to receive data at a default frequency value for all health attributes that are not associated with a non-default frequency value. The frequency for a health attribute and/or the default frequency may be set as any time period, including seconds, minutes, hours, days, weeks, months, years, etc. The cognitive behavioral therapy platform 101 may pull data, at the associated frequency or the default frequency, related to the one or more health attributes from the one or more external systems described above including the personal health and/or fitness tracking systems 102 and user medical devices 105 of the patient. In some embodiments, the cognitive behavioral therapy platform 101 sends alerts to the patient if data related to health attributes or activities are not provided to or received by the cognitive behavioral therapy platform 101 after a threshold amount of time.

In step 705, the cognitive behavioral therapy platform 101 reviews data related to the identified health attributes and activities. In some embodiments, the cognitive behavioral therapy platform 101 is configured to review and analyze the received data after a period of time, which is set based on a user input or a default value. In reviewing and analyzing the received data, the cognitive behavioral therapy platform 101 compares the received data with expected data. As used herein, "expected data" are minimum threshold values that a patient in similar circumstances as the current patient is able to provide for a health attribute of activity. For example, if expected data value for physical activity by a patient in similar circumstances is 1400 steps taken per day, then cognitive behavioral therapy platform 101 reviews and analyzes the received data related to physical activity by comparing it with the expected data for physical activity.

In step 706, the cognitive behavioral therapy platform 101 identifies activities that are troublesome for each health attribute. The cognitive behavioral therapy platform 101 identifies the activities that are troublesome based on the review and analysis of received data. For example, if one of the identified activities is physical activity and the cognitive behavioral therapy platform 101 determines, based on comparison of expected data for physical activity and the received physical activity data, that the received physical activity is worse than the expected physical activity data, then the cognitive behavioral therapy platform 101 identifies physical activity as a troublesome activity. In step 707, the cognitive behavioral therapy platform 101 determines whether there are any sub-activities of the identified activities. An example of activity with sub-activities is calories consumption, where calories consumed may be segmented based on calories consumed from fats, sugars, etc. and calories consumed from proteins, etc. If an activity has sub-activities, then step 708, the cognitive behavioral therapy platform 101 identifies the sub-activities that are troublesome. Identification of sub-activities that are troublesome is performed similar to the identification of the activities that are troublesome. For example, the cognitive behavioral therapy platform 101 may determine that the number of calories consumed from fats and sugars are greater than the expected data and identify calorie consumption from fats and sugars as a troublesome sub-activity.

In step 709, the cognitive behavioral therapy platform 101 generates an initial protocol that includes the troublesome activities for each identified health attribute. The cognitive behavioral therapy platform 101 may search and select the initial protocol from the protocol database 614 using identified health attributes, information of the patients, and then the cognitive behavioral therapy platform 101 may further customize the initial protocol by adding the identified troublesome activities to the initial protocol if the identified activities are not included in the initial protocol. As described above, information of patients includes, but is not limited to, biographical, physiological, geographical information.

In step 710, the cognitive behavioral therapy platform 101 sets performance goals for each identified activities and/or sub-activity for the health attributes. The cognitive behavioral therapy platform 101 determines the performance goals of the activity and/or sub-activities based on population data received for such activities from patients in similar biographical physiological and geographical circumstances who are not subject to same health risk to require the medical intervention as the current patient. As described above, the cognitive behavioral therapy platform is configured to identify patients who are subject to a health risk and those who are not. The cognitive behavioral therapy platform 101 sets the performance goals based on data corresponding to the identified activities from patients that are not subjected to the same health risk. In step 711, the cognitive behavioral therapy platform 101 sets a period of time, after which, the initial protocol will be reviewed by the cognitive behavioral therapy platform 101 and/or the clinician.

In step 712, the cognitive behavioral therapy platform 101 receives and tracks data related to the health attributes and the identified activities and/or sub-activities. As described above, the data related to heath attributes and activities are received at certain frequencies. The frequency may be the default frequency described above or a frequency specified in the protocol. In some embodiments, the cognitive behavioral therapy platform 101 tracks data by determining trend data for the received data. For example, if the activity is physical activity, then the cognitive behavioral therapy platform 101 determines whether the patient is on track to reach the performance goals by projecting the physical activity data at the time of review based on received data. In some embodiments, if the trend data determined by the cognitive behavioral therapy platform 101 indicates that the patient will fail to meet the performance goal, then the cognitive behavioral therapy platform 101 transmits an alert to the patient indicating the projection that the patient will fail to satisfy the performance goal for the activity. In step 713, the cognitive behavioral therapy platform 101 determines whether the set time period for review has elapsed to review of the initial protocol. If the set time period for review has not elapsed, then the cognitive behavioral therapy platform 101 continues with receiving and tracking of health attributes and activities data.

If the set time period for review has elapsed, then the cognitive behavioral therapy platform 101, in step 714, determines whether a threshold number of performance goals are satisfied. The cognitive behavioral therapy platform 101 compares a performance goal of an activity with the data received for the activity and identifies a performance goal as being satisfied if the data received exceeds the performance goal. If a threshold number of the performance goals are not satisfied, then in step 725, shown in FIG. 7C, the cognitive behavioral therapy platform 101 determines whether, for the activities that did not satisfy the performance goal, the patient was within a threshold difference of satisfying the performance goals. For example, if the threshold difference of satisfying performance goals is 2 percent, then the cognitive behavioral therapy platform 101 determines if the received data from the patient by the time of review indicates that the patient was 2 percent away from satisfying the performance goals. The cognitive behavioral therapy platform 101 may determine whether the patient was within the threshold difference of the performance goal at an activity level and identifies activities for which the patient was not within the threshold difference of the performance goal. The cognitive behavioral therapy platform 101 may also determine whether, on average, the patient was within the threshold difference of the performance goals of the activities.

If the performance of the patient is within the threshold difference, then the cognitive behavioral therapy platform 101 maintains the initial protocol and returns to step 712 in step 729. If the cognitive behavioral therapy platform 101 determines that the patient is not within the threshold difference, then in step 727, the cognitive behavioral therapy platform 101 reduces the difficulty of the performance goals and in step 728 generates an easier version of the initial protocol with the performance goals. In step 729, the cognitive behavioral therapy platform 101 returns to step 712.

If threshold number of performance goals is satisfied, then in step 715, the cognitive behavioral therapy platform 101 determines whether to maintain initial protocol. In determining whether to maintain the initial protocol, the cognitive behavioral therapy platform 101 determines whether the performance goals were satisfied within a threshold percentage of satisfying the goals. For example, if the threshold percentage is set at 3 percent, then if the activity data of the patient at the time of review is within 3 percent of the performance goals or the average of all activity data is within 3 percent of the performance goals, then the cognitive behavioral therapy platform determines that the initial protocol should be maintained. In some embodiments, the cognitive behavioral therapy platform 101 may determine whether to maintain the initial protocol at the activity level. For example, if physical activity is within 3 percent and calorie consumption exceeds 3 percent, then the cognitive behavioral therapy platform 101 determines that the performance goals for the physical activity should be maintained and performance goals for calorie consumption should be increased in difficulty.

Figure 7B:
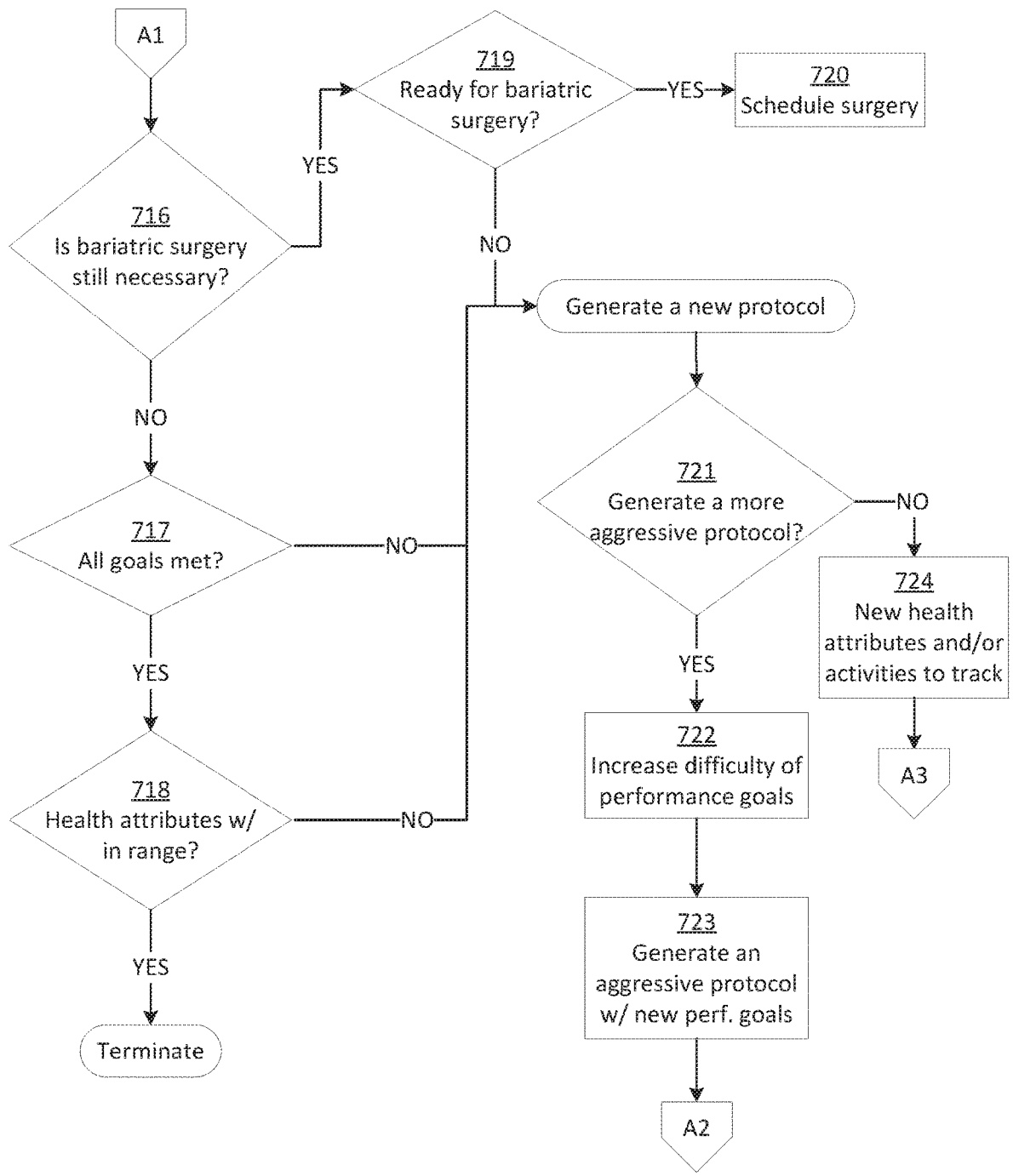
Figure 7C:
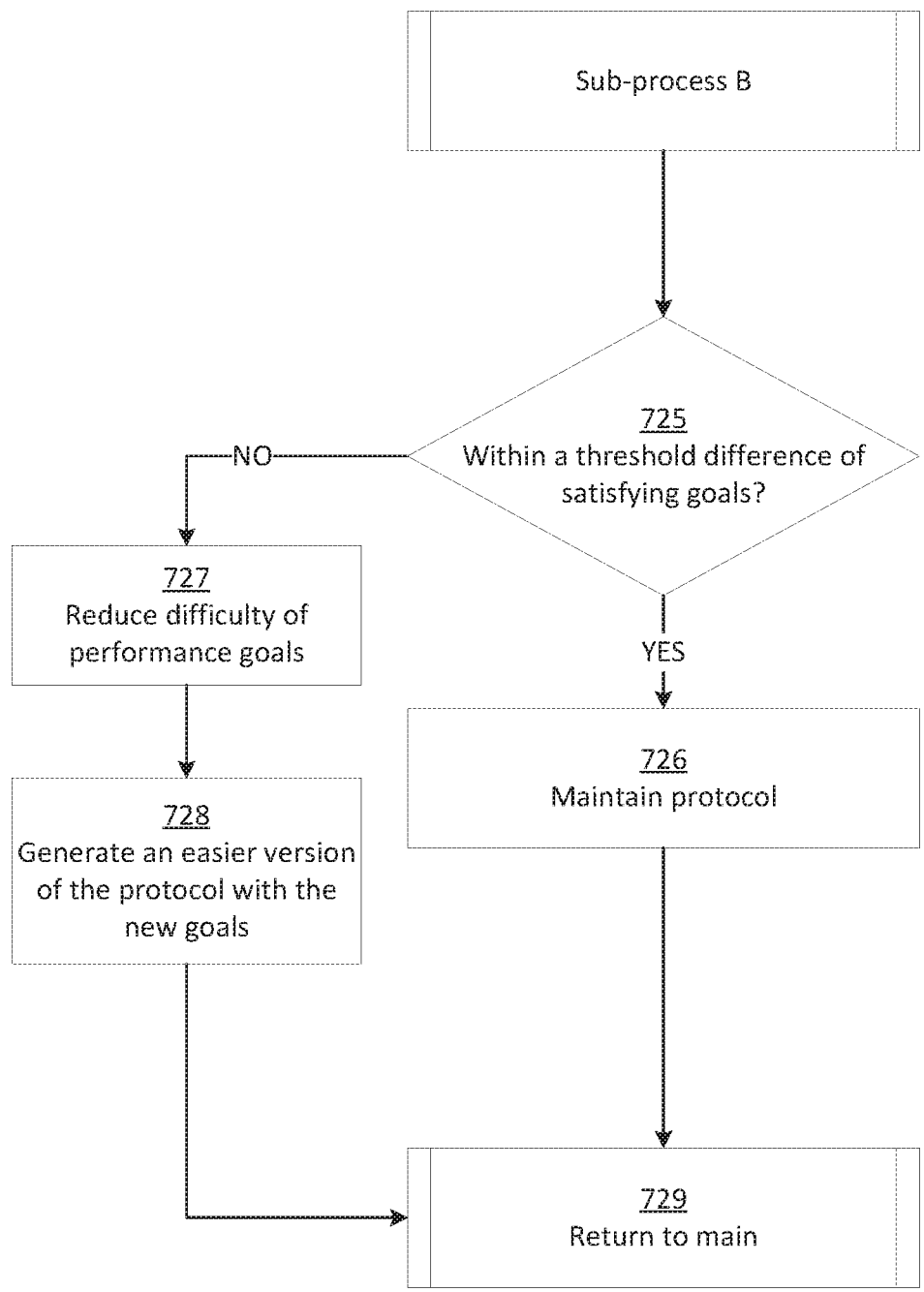

If the performance goals are satisfied by more than the threshold percentage, the cognitive behavioral therapy platform 101, in step 716, shown in FIG. 7B, determines whether the medical intervention is still necessary. An example of such a medical intervention is the bariatric procedure, as shown in FIG. 7. In determining whether a bariatric procedure, the medical intervention, is still necessary, the cognitive behavioral therapy platform 101 determines whether the performance of the patient exceeded the threshold percentage by a threshold margin sufficient to explore alternatives to the bariatric procedure. If the patient exceeded the threshold percentage by the threshold margin, then, in step 717, the cognitive behavioral therapy platform 101 determines whether performances in all of the activities satisfied the performance goals. If the performances in all of the activities did not satisfy the performance goals, then the method 700 moves to step 721 to determine whether to generate a more aggressive protocol.

If the performances in all of the activities did satisfy the performance goals, then the cognitive behavioral therapy platform 101, in step 718, determines whether the health attribute is within an acceptable range. For example, if health attribute is body weight, then the cognitive behavioral therapy platform 101 determines whether the body weight at the time of review is within a threshold range of body weights for a patient of similar biographical circumstance, such as a patient of similar age. If the health attribute is within the acceptable range then the method 700 is terminated the method 700. If the health attribute is not within the acceptable range then the method 700 moves to step 721 to determine whether to generate a more aggressive protocol.

In step 716, if the patient did not exceed the threshold percentage of performances by the threshold margin, then, in step 719, the cognitive behavioral therapy platform 101 determines whether the patient is ready for the medical intervention (e.g., the bariatric procedure). In determining whether the patient is ready for bariatric procedure, the cognitive behavioral therapy platform 101 determines whether the health attribute is within a range for the medical intervention. For example, if the medical intervention is a bariatric procedure and the health attribute is body weight, then the cognitive behavioral therapy platform 101 determines, based on stored rules, whether the body weight of the patient is within a range of body weights such that performance of bariatric procedure will have the greatest impact in further bringing the health attribute within a healthy range. If the patient is ready for the medical intervention, then in step 720, the cognitive behavioral therapy platform 101, utilizing one or more of the medical facility administrative systems 104, schedules the patient for the procedure. If the patient is not ready for the medical intervention, then the method 700 moves to step 721 to determine whether to generate a more aggressive protocol.

In step 721, the cognitive behavioral therapy platform 101 determines whether to generate a more aggressive protocol, based on whether the patient exceeded the threshold percentage by threshold margin, whether all the performance goals were satisfied, whether the health attribute is within a threshold margin of the threshold range, and/or whether a counter indicating number of times performance goals were increased exceeds a threshold count. If the cognitive behavioral therapy platform 101 determines that the patient exceeds the threshold percentage by the threshold margin, that all performance goals were satisfied, and the counter is less than a threshold count, then the cognitive behavioral therapy platform 101, in step 722, increases difficulty of the performance goals and in step 723, generates an aggressive protocol with the new performance goals and the method moves to step 712 to receive and track data in view of the new performance goals.

If the cognitive behavioral therapy platform 101 determines that the patient exceeds the threshold percentage by the threshold margin, that all performance goals were satisfied, and that the counter is not less than a threshold count, or if the cognitive behavioral therapy platform 101 determines that the patient exceeds the threshold percentage by the threshold margin, but all performance goals are not satisfied, then in step 724, the cognitive behavioral therapy platform 101 identifies new health attributes and/or activities that are not included in the initial protocol to track and the method moves to step 703 to begin the investigatory phase of the new health attributes and/or activities of the patient.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an example," "in examples," "in some examples," "in an embodiment," "in embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C".

The systems described herein may also utilize one or more controllers to receive various information and transform the received information to generate an output. The controller may include any type of computing device, computational circuit, or any type of processor or processing circuit described herein. The controller may include multiple processors and/or multicore central processing units (CPUs) and may include any type of processor described herein. The controller may also include a memory to store data and/or instructions that, when executed by the one or more processors, causes the one or more processors to perform one or more methods and/or algorithms.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory described herein. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A system for cognitive behavioral therapy, comprising:
    a display presenting a user interface; and
    a computing device coupled to the display and including:
        a processor; and
        a memory coupled to the processor and storing instructions which, when executed by the processor, cause the system to:
            display, via the user interface, a first set of data related to a health attribute in a first graphical item;
            display, via the user interface, a second set of data related to the health attribute in a second graphical item;
            overlay, via the user interface, the first graphical item at least partially over the second graphical item;
            generate, in response to overlaying the first graphical item at least partially over the second graphical item, a third set of data at least partially based on associating the first set of data with the second set of data using at least one set of rules that establishes a relationship between the first set of data and the second set of data; and
            display, via the user interface, the third set of data in a third graphical item.

2. The system, according to claim 1, wherein the instructions, when executed by the processor, cause the system to receive the first set of data and the second set of data over the same period of time.

3. The system according to claim 1, wherein the instructions, when executed by the processor, cause the system to receive input via the user interface to move the first graphical item on the user interface.

4. The system according to claim 1, wherein the instructions, when executed by the processor, cause the system to display a graphical button on the first graphical item, the graphical button configured to facilitate movement of the first graphical item on the user interface.

5. The system according to claim 4, wherein the instructions, when executed by the processor, cause the system to receive input via the user interface to use the graphical button to overlay the first graphical item at least partially over the second graphical item.

6. A method for cognitive behavioral therapy, comprising:
    displaying, via a user interface coupled to a computing device, a first set of data related to a health attribute in a first graphical item;
    displaying, via the user interface, a second set of data related to the health attribute in a second graphical item;
    overlaying, via the user interface, the first graphical item at least partially over the second graphical item;
    generating, in response to overlaying the first graphical item at least partially over the second graphical item, a third set of data at least partially based on associating the first set of data with the second set of data; and
    displaying, via the user interface, the third set of data in a third graphical item.

7. The method according to claim 6, further comprising receiving the first set of data and the second set of data over the same period of time.

8. The method according to claim 6, further comprising receiving input via the user interface to move the first graphical item on the user interface.

9. The method according to claim 6, further comprising displaying a graphical button on the first graphical item, the graphical button configured to facilitate movement of the first graphical item on the user interface.

10. The method according to claim 9, further comprising receiving input via the user interface to use the graphical button to overlay the first graphical item at least partially over the second graphical item.

11. The method according to claim 6, wherein generating the third set of data includes using at least one set of rules that establishes a relationship between the first set of data and the second set of data.

12. The method according to claim 6, wherein the first set of data includes measurements corresponding to a first activity associated with the health attribute and the second set of data includes data corresponding to a second activity associated with the health attribute.

13. The method according to claim 6, further comprising receiving the first set of data at a first frequency and receiving the second set of data at a second frequency different than the first frequency.

14. The method according to claim 6, further comprising displaying a fourth graphical item that displays information about a total number of patients and health status for the total number of patients.

15. The method according to claim 14, further comprising displaying a fifth graphical item that displays a number of patients from the total number of patients who are at risk of experiencing a health-related event and an associated color.

16. The method of claim 14, further comprising displaying a sixth graphical item that displays a number of patients from the total number of patients who are not at risk of experiencing a health-related event and an associated color.

17. A method for generating protocols for medical intervention, comprising:

displaying, via a user interface coupled to a computing device, a first set of data related to a health attribute in a first graphical item;

displaying, via the user interface, a second set of data related to the health attribute in a second graphical item;

moving the first graphical item at least partially over the second graphical item via the user interface;

generating, in response to moving the first graphical item at least partially over the second graphical item, a third set of data at least partially based on associating the first set of data with the second set of data; and displaying, via the user interface, the third set of data in a third graphical item.

18. The method according to claim 17, further comprising displaying, via the user interface, a fourth graphical item that displays information about a total number of patients and health status for the total number of patients.

19. The method according to claim 18, further comprising displaying, via the user interface, a fifth graphical item that displays a number of patients from the total number of patients who are at risk of experiencing a health-related event and an associated color.

20. The method of claim 18, further comprising displaying, via the user interface, a sixth graphical item that displays a number of patients from the total number of patients who are not at risk of experiencing a health-related event and an associated color.

\* \* \* \* \*